(12) United States Patent
McGarvey et al.

(10) Patent No.: US 11,605,470 B2
(45) Date of Patent: Mar. 14, 2023

(54) TELE-HEALTH NETWORKING, INTERACTION, AND CARE MATCHING TOOL AND METHODS OF USE

(71) Applicant: Telemedicine Provider Services, LLC, Boulder, CO (US)

(72) Inventors: Kevin McGarvey, Boulder, CO (US); Michael Zdepski, Boulder, CO (US); Tom Piekos, Boulder, CO (US); Jason Sperling, Boulder, CO (US); David Carroll, Boulder, CO (US); Stirling Olson, Boulder, CO (US)

(73) Assignee: Telemedicine Provider Services, LLC, Boulder, CO (US)

( * ) Notice: Subject to any disclaimer, the term of this patent is extended or adjusted under 35 U.S.C. 154(b) by 874 days.

(21) Appl. No.: 16/509,683

(22) Filed: Jul. 12, 2019

(65) Prior Publication Data

US 2020/0020454 A1    Jan. 16, 2020

Related U.S. Application Data

(60) Provisional application No. 62/848,900, filed on May 16, 2019, provisional application No. 62/696,881, filed on Jul. 12, 2018.

(51) Int. Cl.
*G10L 15/22* (2006.01)
*G16H 80/00* (2018.01)
(Continued)

(52) U.S. Cl.
CPC ......... *G16H 80/00* (2018.01); *G06Q 30/0282* (2013.01); *G06V 40/174* (2022.01); *G10L 15/22* (2013.01); *G10L 2015/227* (2013.01)

(58) Field of Classification Search
CPC ........ G16H 80/00; G16H 10/20; G16H 10/60; G06Q 30/0282; G06Q 30/02;
(Continued)

(56) References Cited

U.S. PATENT DOCUMENTS 9,298,766 B2 *  3/2016  Kozloski ................. G06N 5/04
2014/0278506 A1 *  9/2014  Rogers ................... G16H 15/00
705/2

(Continued)

*Primary Examiner* — Huyen X Vo
(74) *Attorney, Agent, or Firm* — James A. Sheridan; Sheridan Law, LLC

(57) ABSTRACT

An integrated tele-health networking, interaction, and care-matching tool for tele-health services may include a tele-health operations server in communication with patient, provider, matching, and interaction databases. A management engine running on the server may execute a database management module, a rule module, and a GUI module configured to display a GUI having a plurality of preconfigured screens at a plurality of user terminals. In operation, the management engine implements a referral-based care network that connects a patient with healthcare providers, non-medical-professional caregivers, advocates, and friends or family via the user terminals. The management engine also receives rating and personality assessment information from the patient and records interaction variables and emotional reaction information from care interactions and uses that information to respectively match the patient with an optimal healthcare provider(s) selected from the network and to determine an empathy meter score for the care interaction. Other embodiments are disclosed.

19 Claims, 21 Drawing Sheets

(51) Int. Cl.
*G06Q 30/0282* (2023.01)
*G06V 40/16* (2022.01)

(58) Field of Classification Search
CPC .............. G06V 40/174; G06V 40/16; G10L 2015/227; G10L 15/22; G10L 25/63
See application file for complete search history.

(56) References Cited

U.S. PATENT DOCUMENTS

| | | | |
|---|---|---|---|
| 2016/0005004 A1* | 1/2016 | Trabue | G06Q 10/1095 705/7.19 |
| 2018/0110460 A1* | 4/2018 | Danson | A61B 5/14542 |
| 2019/0122409 A1* | 4/2019 | Meadows | G06N 3/08 |

* cited by examiner

|  | Pitch (Hz) | SPL (dB) | Timbre ascend time (s) | Timbre descend time (s) | Time gaps between word (s) |
|---|---|---|---|---|---|
| Speech Sample 1 | 1248 Hz | Gain -50 dB | 0.12 s | 0.11 s | 0.12 s |
| Speech Sample 2 | 1355 Hz | Gain -48 dB | 0.06 s | 0.05 s | 0.12 s |

|  | Pitch (Hz) | SPL (dB) | Timbre ascend time (s) | Timbre descend time (s) | Time gaps between word (s) |
|---|---|---|---|---|---|
| Speech Sample 1 | 1541 Hz | Gain -30 dB | 0.13 s | 0.10 s | 0.09 s |
| Speech Sample 2 | 1652 Hz | Gain -29 dB | 0.06 s | 0.04 s | 0.10 s |

|  | Pitch (Hz) | SPL (dB) | Timbre ascend time (s) | Timbre descend time (s) | Time gaps between word (s) |
|---|---|---|---|---|---|
| Speech Sample 1 | 1443 Hz | Gain -46 dB | 0.13 s | 0.09 s | 0.13 s |
| Speech Sample 2 | 1560 Hz | Gain -44 dB | 0.07 s | 0.04 s | 0.14 s |

| | Post Interaction | | | | |
|---|---|---|---|---|---|
| | Survey | 10 Star rating system by patient | 8 | 8 | 4 |
| | HCAPS | MIPS | | | |
| Payer | Claims | | | | |
| | 1 month | Cost of care | $1,000 | $500 | $100,000 |
| | 3 months | Cost of care | $3,000 | $500 | $200,000 |
| | 12 months | Cost of care | $10,000 | $1,000 | $225,000 |
| Clinical Data | Acute Illness | | | | |
| | Chronic Illness | | | | |
| | Labs | | | | |
| | Vitals | | | | |
| Social Data | Zip Code | | | | |
| | Smoking | | | | |
| | Drinking | | | | |
| | Drugs | | | | |
| | Family | | | | |
| | Ethnicity | | | | |

FIG. 16B

|  |  | End Result Did you feel cared for? | |
|---|---|---|---|
|  |  | Phase 1 Output | Phase 1 Empathy Meter |
| Patient 1 | Front Desk Intro Experience | 5 | 3 |
|  | Introduction | 8 | |
|  | Anxiety Reduction | 4 | |
|  | Understanding | 3 | |
|  | Confidence | 4 | |
|  | Closing | 3 | |
| Patient 2 | Front Desk Intro Experience | 5 | 10 |
|  | Introduction | 9 | |
|  | Anxiety Reduction | 9 | |
|  | Understanding | 9 | |
|  | Confidence | 7 | |
|  | Closing | 8 | |
| Patient 3 | Front Desk Intro Experience | 5 | 3 |
|  | Introduction | 5 | |
|  | Anxiety Reduction | 5 | |
|  | Understanding | 5 | |
|  | Confidence | 5 | |
|  | Closing | 5 | |

FIG. 16C

TELE-HEALTH NETWORKING, INTERACTION, AND CARE MATCHING TOOL AND METHODS OF USE

REFERENCE TO PRIOR PATENT APPLICATIONS

This application claims the benefit under 35 U.S.C. 119 (e) of U.S. Provisional Patent Application No. 62/696,881, filed Jul. 12, 2018 by Kevin McGarvey, Michael Zdepski, Tom Piekos, Jason Sperling, David Carroll, and Stirling Olson for "TELE-HEALTH NETWORKING, INTERACTION, AND CARE MATCHING TOOL AND METHODS OF USE" and 62/848,900, filed May 16, 2019 by Kevin McGarvey, Michael Zdepski, Tom Piekos, Jason Sperling, David Carroll, and Stirling Olson for "TELE-HEALTH NETWORKING, INTERACTION, AND CARE MATCHING TOOL AND METHODS OF USE," the entirety of each of which patent applications is hereby incorporated herein by reference.

BACKGROUND

It can be challenging to have clear, easy communication between patients, their loved ones, and their care professionals, especially on complex care issues when parts of the care team are separated from each other. This lack of communicative ability leads to conservative clinical decision-making and, at times, a lack of patient and family engagement, keeping patients from being successfully managed in the outpatient setting when an illness is severe or presents a high degree of risk.

Further, current mechanisms for matching patients with an appropriate healthcare provider or providers are antiquated and oftentimes involve a simple look-up tool or search for any available or appropriate provider in the patient's geographical area, without considering, or matching to, the most advantageous or optimal provider for the patient and/or the patient's particular circumstances. Moreover, once the patient is matched with or has selected a healthcare provider or providers, the provision of healthcare services is often perceived as a simple transaction, lacking empathetic emotional connections between the patient and the care provider(s).

In addition, tele-health technologies currently are sold for a price to healthcare practitioners, who then must pass those expenses to patients via out-of-pocket expenses or copays. This model has resulted in fewer established physicians integrating tele-health services into their local care communities, resulting in the sluggish disseminated adoption of a universal tele-health platform across care communities.

SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

One embodiment provides an integrated tele-health networking, interaction, and care-matching system. The system may include: (1) a tele-health operations server operating one or more processors; (2) a patient database, a provider database, a matching database, and an interaction database; and (3) a management engine running on the tele-health operations server, the management engine executing a database management module, a rule module including a network module, a care match module, an empathetic interaction module, and a graphical user interface (GUI) module configured to display a GUI having a plurality of preconfigured, interactive screens to users operating at least a healthcare provider terminal, a patient terminal, a caregiver terminal, an advocate terminal, and a friend and family terminal, the management engine: (a) receiving, via one or more emotional data elicitation tools associated with at least one of the healthcare provider terminal and the patient terminal, recorded interaction data for a patient reflecting a care interaction between a healthcare provider and the patient; (b) determining, based on the recorded interaction data, emotional interaction information reflecting a state of mind of the patient during the care interaction; (c) based on a plurality of predefined empathetic criteria, rating the emotional reaction information; and (d) based on the rating of the emotional reaction information, determining a real-time empathy meter score for the care interaction.

Another embodiment provides a system for determining an empathetic quality of a care interaction between a patient and a healthcare provider. The system may include: (1) one or more emotional data elicitation tools associated with at least one of a patient terminal and a provider terminal; (2) one or more databases storing patient data, provider data, care matching data, and care interaction data; and (3) an empathetic interaction module running on an operations server and in communication with the patient terminal, the provider terminal, and the one or more of the databases, the empathetic interaction module: (a) receiving, from the one or more of the emotional data elicitation tools, a stream of care interaction data recorded during the care interaction; (b) determining, from the stream of the care interaction data, an emotional reaction of the patient during the care interaction; (c) rating the emotional reaction of the patient on a sliding scale from a least empathy experienced to a most empathy experienced; (d) determining, based on the rating of the emotional reaction of the patient, one or more empathy meter scores reflecting the empathetic quality of the care interaction for the patient; and (e) displaying the one or more of the empathy meter scores at one or more of the patient terminal and the provider terminal.

Yet another embodiment provides a method of scoring a healthcare interaction for empathy offered to a patient by a healthcare provider. The method may include the following steps: (1) providing a tele-health operations server in communication with a storage system, a patient terminal, and a healthcare provider terminal, the tele-health operations server running a management engine that executes an empathetic interaction module, a care match module, and a graphical user interface (GUI) module; (2) receiving, via one or more emotional data elicitation tools associated with at least one of the patient terminal and the healthcare provider terminal, a stream of care interaction data recorded during the healthcare interaction, the care interaction data comprising one or more of a voice tone, a voice pitch, a voice pitch range, a voice volume, a speaking speed, a facial expression, and a segment of discussion content; (3) comparing, via the empathetic interaction module, the stream of the care interaction data recorded during the healthcare interaction with a plurality of statistical data associated with one or more known human emotional states to associate one or more emotional reactions of the patient to the healthcare interaction with the stream of the care interaction data; (4) rating, via the empathetic interaction module, the one or more of the emotional reactions on a sliding scale in which a lowest rating is associated with a least empathetic interaction and a highest rating is associated with a most empathetic interaction; and (5) determining, via the empathetic interaction module and based on the rating of the one or more of the emotional reactions, one or more empathy meter scores reflecting the empathy felt by the patient from the healthcare provider.

Other embodiments are also disclosed.

Additional objects, advantages and novel features of the technology will be set forth in part in the description which follows, and in part will become more apparent to those skilled in the art upon examination of the following, or may be learned from practice of the technology.

BRIEF DESCRIPTION OF THE DRAWINGS

Non-limiting and non-exhaustive embodiments of the present invention, including the preferred embodiment, are described with reference to the following figures, wherein like reference numerals refer to like parts throughout the various views unless otherwise specified. Illustrative embodiments of the invention are illustrated in the drawings, in which:

FIGS. 15A-15C provide statistical charts reflecting initial voice intonation baselines, with changes in voice intonation that statistically suggest different emotional states associated with known intonation responses, including a normal emotional state, an angry emotional state, and a panicked emotional state, respectively;

FIGS. 16A-16C provide an exemplary neural network framework through which emotional reaction information resulting from recorded interaction data during a care experience is used to determine an empathy meter score for the care experience using the empathetic interactions subsystem of FIG. 1.

DETAILED DESCRIPTION

Embodiments are described more fully below in sufficient detail to enable those skilled in the art to practice the system and method. However, embodiments may be implemented in many different forms and should not be construed as being limited to the embodiments set forth herein. The following detailed description is, therefore, not to be taken in a limiting sense.

Various embodiments of the systems and methods described herein generally relate to connecting healthcare professionals, care advocates, caregivers, family members, friends, and patients virtually and in-person on an intuitive communication care network platform that helps people feel cared for by better matching patients and care providers while optimizing empathetic emotional connections in healthcare and other service industries. The disclosed system allows telemedicine to go deeper in delivering medical care. Through seamless, user friendly communication channels, patients and their care teams can better address complicated care scenarios and illnesses. In complex care populations, the care network platform can enable a divergent team of patient advocates and care professionals to better communicate and more effectively care for a patient to improve clinical outcomes and reduce wasteful, fragmented episodic care.

Figure 1A:
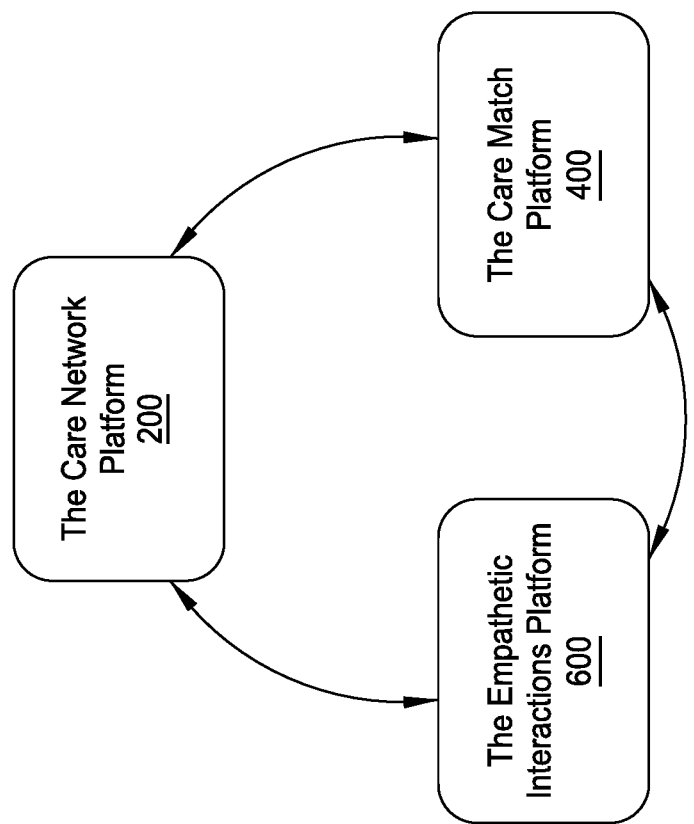
FIG. 1A provides a functional diagram of a three-part tele-health networking, interaction, and care-matching system including a care network subsystem, a care match subsystem, and an empathetic interactions subsystem.

More specifically, the disclosure describes a tele-health networking, interaction, and care-matching system 50 that includes three complimentary subsystems or platforms, graphically depicted in FIG. 1A: (1) a care network platform or subsystem 200 that connects patients with all of the stakeholders invested in their optimal care, including any number of healthcare providers, non-medical-professional caregivers, health advocates, family members, and/or friends; (2) a care match subsystem or platform 400 that combines a ratings and reputation tool with a personality assessment tool to assist in matching patients with healthcare providers having aligned "personas," and therefore, giving the providers the highest likelihood of making the patients feel the most cared for; and (3) an empathetic interactions subsystem or platform 600 that supplements the care match subsystem to facilitate the care match process by analyzing actual provider-patient care interactions for emotional cues that the interaction is perceived by the patient as empathetic, compassionate, and caring and collecting objective data relating to the care interaction to further facilitate care matches for the patient. All three platforms/subsystems interact to optimize the quality and expansion of each interrelated platform, and the data procured from each platform helps inform the others on optimizing care interactions, matching patients and providers, and determining how and where to invite new providers into the network.

Figure 1B:
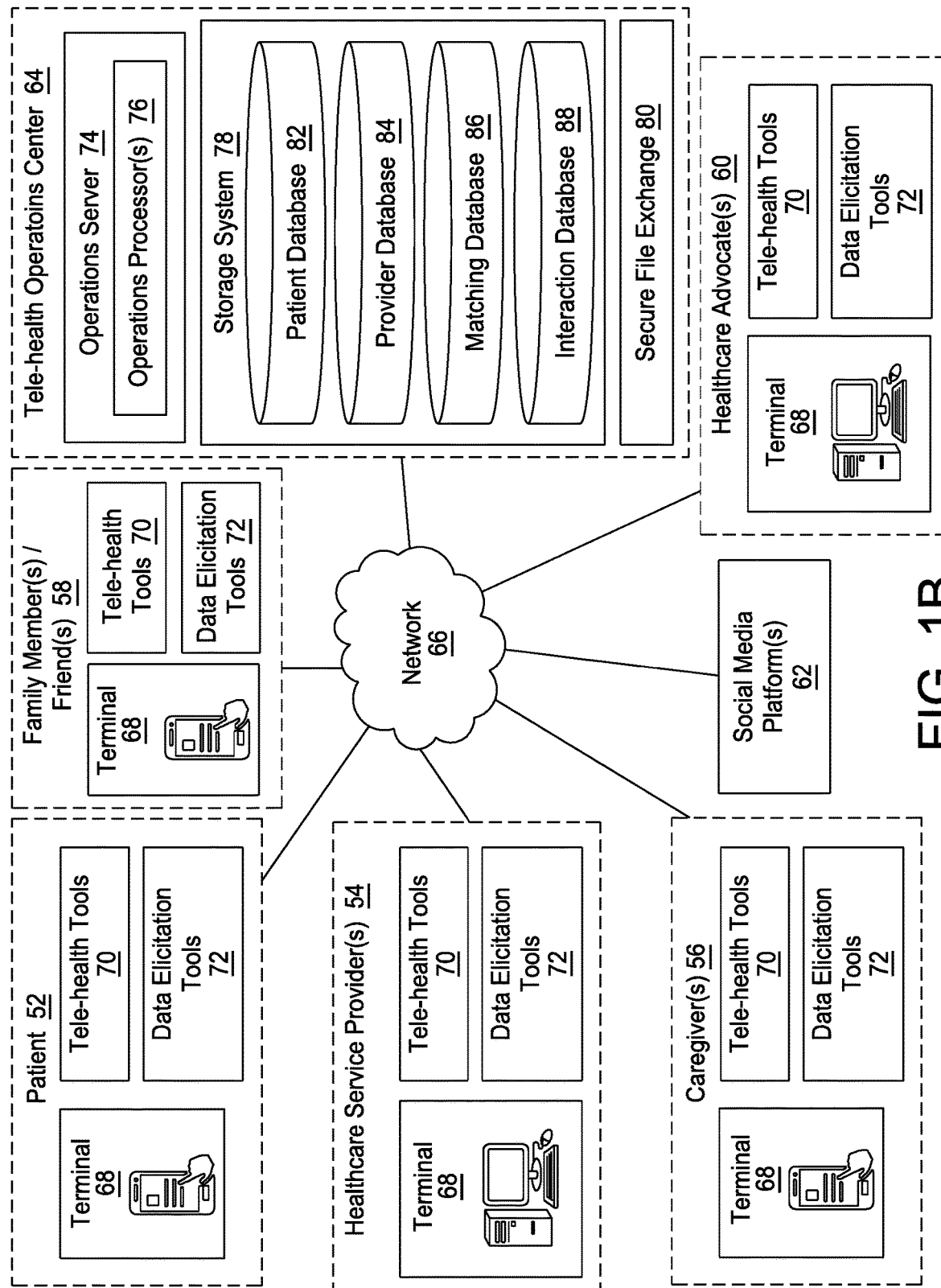
FIG. 1B provides a block diagram of an illustrative environment where various tele-health systems and methods described herein are implemented according to some embodiments.
Figure 1C:
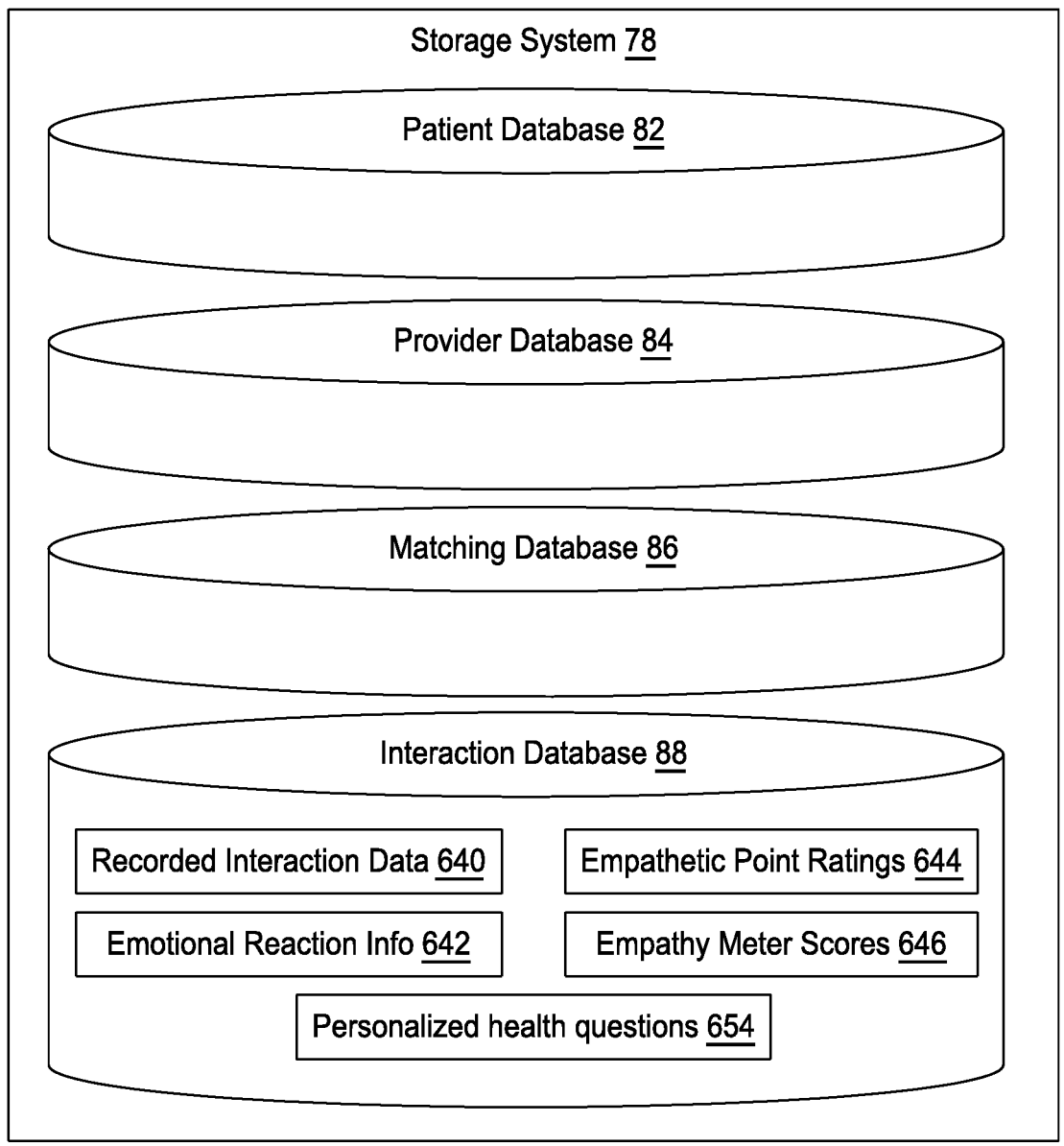
FIG. 1C provides a block diagram further detailing a storage system of FIG. 1B.

FIGS. 1B-1C provide block diagrams depicting an illustrative environment and device ecosystem within and through which the care network, care match, and empathetic interactions subsystems 200, 400, 600 and associated techniques described herein may be implemented according to some embodiments. As shown in FIG. 1B, a patient 52 may be communicatively connected with one or more healthcare providers 54, caregivers 56, personal contacts such as family members and/or friends 58, healthcare advocates 60, social media platforms 62, and a tele-health operations center 64 via a network 66 of secure communication channels.

In some embodiments, each of the patients 52, the healthcare providers 54, the caregivers 56, the family members/friends 58, and the healthcare advocates 60 may operate a network-enabled terminal 68 configured to securely compile and transmit information to and from other system components. Each of the terminals 68 may be any appropriate network-enabled mobile or desktop user device such as, for example, a desktop computer, laptop computer, tablet computer, smartphone, or the like. Each of the user terminals 68 may incorporate or access a communication system that provides network communication abilities. An exemplary communication system may include one or more analog switches, servers, IP gateways, PBX systems, etc. For example, in some embodiments, the communication system may be operable to provide communications through the network 66, which may include, for example, the Internet. Additionally or alternatively, the network may include wireless cellular networks or the like.

In addition, the user terminals 68 may each be equipped with or operatively coupled to a variety of HIPAA-compliant, remote collaboration, tele-health tools 70 as appropriate and/or desired. The tele-health tools 70 may provide the modalities for telepresence healthcare interactions and a means of providing data to and communicating with system components. Such tele-health tools 70 may include, for example, secure chat and messaging tools, video conferencing tools, voice-over Internet technologies, and/or file sharing exchanges. In addition, the user terminals 68 and/or the tele-health operations center 64 may also be equipped with and/or operatively coupled to a variety of software and/or hardware data detection or elicitation tools 72 that enable medical professionals to collect, store, and categorize patient data such as physical patient responses or reactions during virtual or in-person care interactions. Such data elicitation equipment 72 may include, for example, geographic information systems (GISs), voice recognition or recording tools, and/or facial and body language recognition and/or recording tools.

The tele-health operations center 64 may be communicatively coupled with the user terminals 68 operating at the patient 52, the healthcare service provider(s) 54, the caregiver(s) 56, the healthcare advocate(s) 60, and the family member(s)/friend(s) 58. In some embodiments, the tele-health operations center 64 may include one or more operations servers 74 operating one or more operations processors 76, as well as a storage system 78 and a secure file exchange 80.

The storage system 78 may include one or more HIPAA-compliant database or databases, as detailed in FIGS. 1B-1C. In one embodiment, the storage system 78 may include a HIPAA-compliant patient database 82, a HIPAA-compliant provider database 84, a HIPAA-compliant matching database 86, and a HIPAA-compliant interactions database 88. Each of the patient, provider, matching, and interactions databases 82, 84, 86, 88 may be communicatively coupled with the operations server 74 running the operations processors 76, as shown in the schematic of FIG. 1B, and may store any appropriate data and/or information required to implement the care network subsystem or platform 200, the care match subsystem or platform 400, and the empathetic interactions subsystem or platform 600.

Generally speaking, the databases 82, 84, 86, 88 may include any suitable type of application or data structure that may be configured as a data repository. For example, the databases may be configured as relational databases that include one or more tables of columns and rows that may be searched or queried according to a query language, such as a version of Structured Query Language (SQL). Alternatively, the databases may be configured as structured data stores that include data records formatted according to a markup language, such as a version of eXtensible Markup Language (XML). In other embodiments, the databases may be implemented using arbitrarily or minimally structured data files managed and accessible through any suitable type of application or the databases may be non-relational or NoSQL databases. The HIPAA-compliant databases 82, 84, 86, 88 may also be decentralized and implemented via distributed ledger blockchain technology.

The patient, provider, matching, and interactions databases 82, 84, 86, 88, as well as the operations server 74 and processors 76 may be co-located at the tele-health operations center 64. In some embodiments, these components, or sub-components thereof, may be combined or distributed in any appropriate manner across multiple locations and/or distributed computing platforms.

Figure 2:
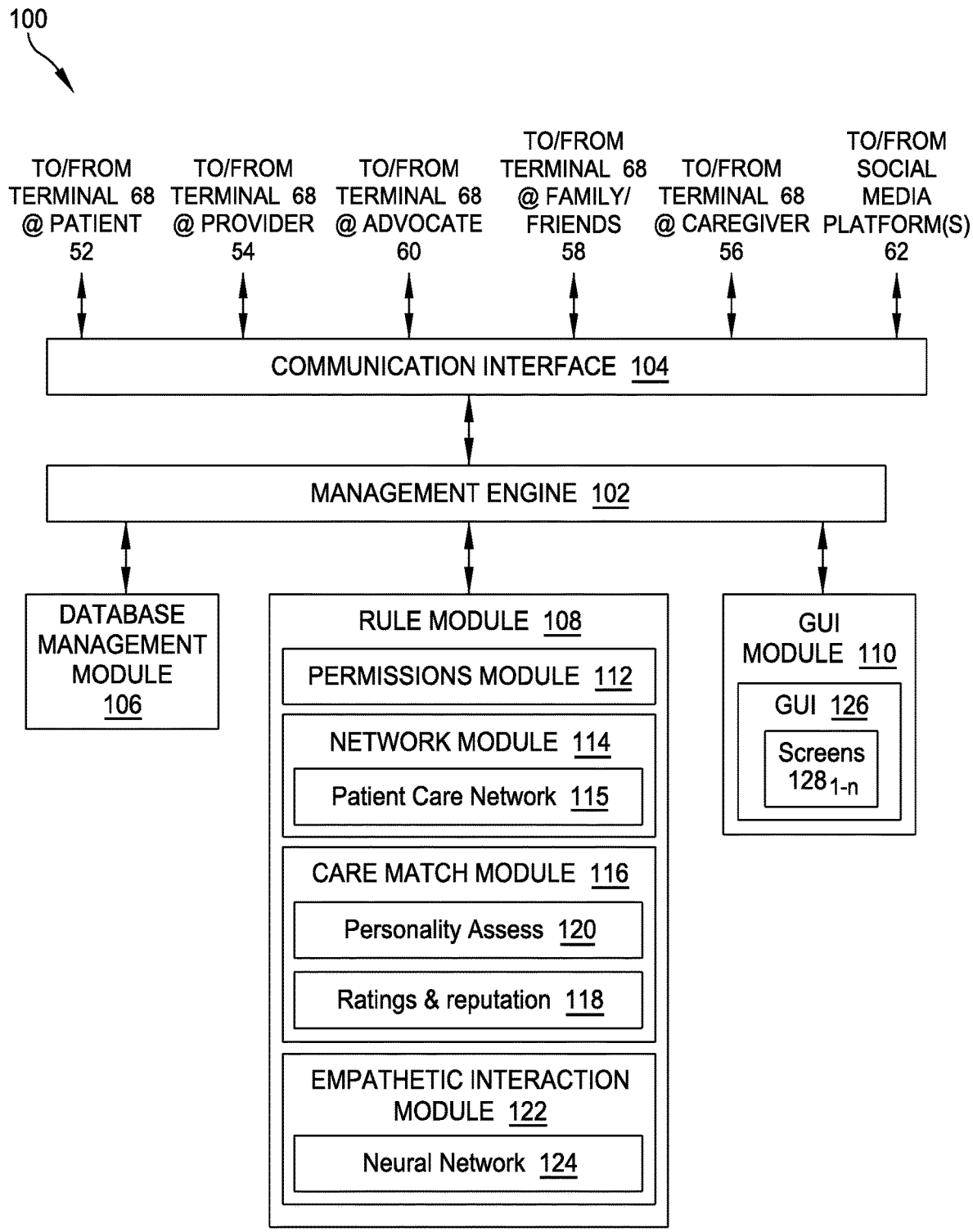
FIG. 2 provides a block diagram depicting illustrative tele-health networking, interaction, and care-matching software according to some embodiments.

FIG. 2 provides a functional block diagram depicting illustrative networking, care matching, and empathetic interaction software 100 according to some embodiments. In various implementations, such software 100 may be executed by the operating processors 76 of the tele-health operations center 64. As shown, a management engine 102 may be coupled to a communication interface 104, a database management module 106, a rule module 108, and a graphical user interface (GUI) module 110. In turn, the communication interface 104 may be communicatively coupled with the user terminals 68 operating at the patient 52, the healthcare provider(s) 54, family/friends 58, the caregiver(s) 56, and the healthcare advocate(s) 60. The communication interface 104 may also connect with one or more of the existing social media platforms 62.

The management engine 102 may be configured to perform a variety of operations related to implementing the care network platform 200 of patients 52, healthcare providers 54, advocates 60, caregivers 56, friends/family 58, and social media platforms 62, as well as the care matching subsystem 400 for matching the patients 52 with the optimal providers 54, and the empathetic interactions subsystem 600 for ensuring empathetic care interactions and enhancing the care matching subsystem 400 with recorded care interaction data, empathetic ratings, emotional reaction information, and empathy meter scores that are collected/observed and/or determined during actual patient-provider interactions, as detailed below.

The communication interface 104 may enable the networking, care matching, and empathetic interaction software 100 to securely exchange information with other systems and/or system components via the network 66, including the patient, provider, advocate, family/friends, and caregiver terminals 68, as well as the one or more social networking platforms 62. In some embodiments, the communication interface 104 may be configured to transmit and/or receive information using secure socket layer (SSL) encryption. Additionally or alternatively, other connections may also be used, such as, for example, XML file transmission utilizing file transfer protocol (FTP), hypertext transfer protocol (HTTP) POST transactions, or other data transmission protocols. The communication interface 104 may further include any of a variety of standardized application programming interfaces (APIs) configured to allow different software programs to communicate (e.g., to request services and respond to such requests) in an autonomous, web-based, and/or platform-independent manner. For example, the user terminal 68 operated by the patient 52 may choose or be operated to expose certain data (e.g., patient surveys, patient preferences, assessment information) via a HIPAA compliant, secured web interface. The communication interface 104 may then access the exposed data and/or functions via the appropriate API(s).

The database management module 106 may include any suitable database management system (DBMS) or application configured to manage the creation, maintenance, and use of the stored data/databases 82, 84, 86, 88 of FIGS. 1B-1C. The rule module 108 may include one or more sets of rules, in any suitable format, that provide a framework for the administration of the three subsystems discussed above, including the care network platform 200, the care matching subsystem 400, and the empathetic interactions subsystem 600, as described in further detail below.

For example, the rule module 108 may include a permissions module 112 that instructs connectivity and privacy across the various user terminals 68 and social networking platforms 62, including permissions defined at the role, group, and/or user levels to determine system access to various system software modules and content. The rule module 108 may also include a network module 114 including instructions pertaining to the implementation of the tele-health care network platform 200, including a personal patient care network 115 for each of the enrolled patients 52, across the various terminals 68 and the social media platforms 62. The rule module 108 may also include a care match module 116 having instructions relating to matching patients 52 with the optimal provider(s) 54, including instructions for implementing a ratings-and-reputation system 118 and a patients-and-providers personality assessment 120. In addition, embodiments of the rule module 108 may include an empathetic interaction module 122 implementing a neural network module 124 configured to provide real-time analysis regarding actual tele-health interactions and whether they result/resulted in the patients 52 feeling cared for and to augment and automate the care match process and analysis using the variety of data detection and/or elicitation tools 72 such as geographic information systems (GISs), voice recognition tools, and facial recognition tools to collect care interaction data and provide real-time feedback regarding the actual tele-health interactions, as detailed below in relation to FIGS. 12-17.

The GUI module 110 may be configured to provide, for example, a web-based user interface (WUI) that implements JAVA®, AJAX®, ADOBE FLEX®, MICROSOFT.NET® or the like, a native mobile application interface such as iOS and Android, or similar technologies to provide real-time user control from any appropriate terminal 68. In other cases, the GUI module 110 may implement a command line interface, an application interface, or another suitable interface using non-web-based technologies.

In various embodiments, a GUI 126 may be displayed to system users via the GUI module of FIG. 2. The GUI 126 may be operable to display information and/or receive commands from the user(s). In various implementations, the GUI 126 may be displayed, via a number of appropriate preconfigured and interactive screens $128_{1-n}$ displayed at the user terminals 68 operating at the patient 52, the healthcare provider 54, the caregiver 56, the advocate 60, and/or family members/friends 58 via the communication interface 104 and the network 66. Numerous exemplary preconfigured and interactive screens $128_{1-n}$ associated with the care network subsystem 200, the care match subsystem 400, and the empathetic interactions subsystem 600 are discussed below in relation to FIGS. 3A-3B, 5-9, 11, and 13.

A browser or application window displayed on any of the user terminals 68 may be configured to display text content, image content, input features, navigable links, etc. of the preconfigured screens $128_{1-n}$ of the GUI 126. Each preconfigured screen $128_{1-n}$ may include any appropriate type of content in various combinations, and the screen(s) $128_{1-n}$ displayed to the users may be specific to the viewing platform. For example, the screen(s) $128_{1-n}$ presented at the terminal 68 operated by the provider 54 may differ from the screen(s) $128_{1-n}$ shown at the terminal 68 operated by the patient 52, which may differ from the screen(s) $128_{1-n}$ shown at the terminal 68 operated by the advocate 60, etc., depending on a variety of factors including, for example, the type of information to be collected or transmitted, security concerns, user permissions, and so on.

The content of the GUI screens $128_{1-n}$ may be interspersed or combined in any suitable fashion according to the capabilities of the browser and language used to implement the GUI 126, and may be displayed in any suitable area of the browser or application window. In some embodiments, the window may be generated and managed by a web browser such as, for example, MICROSOFT EXPLORER®, FIREFOX®, SAFARI®, CHROME®, etc., implemented from the tele-health operations center 64.

In various embodiments, the modules shown in FIG. 2 may represent sets of software routines, logic functions, and/or data structures that are configured to perform specified operations. Although these modules are shown as distinct logical blocks, in other embodiments, at least some of the functionality provided by these modules may be combined into fewer blocks or parceled into additional blocks. Conversely, any given one of the modules may be implemented such that its functionality is divided among two or more logical blocks. Moreover, although shown with a particular configuration, in other embodiments these various modules may be rearranged in other suitable ways.

The various systems and components shown in FIGS. 1A-1C and 2 may allow the implementation of the three subsystems discussed above—the care network subsystem or platform 200, the care match subsystem or platform 400, and the empathetic interactions subsystem or platform 600—including the execution of (1) methods relating to building the patient's personal care network 115 that includes a variety of stakeholders beyond the patient 52 and the healthcare provider 54, and that leverages social media platforms 62, to interconnect the patient 52 with all of the people and/or organizations that are integral to the patient's optimal care and to interconnect patients, providers, and other stakeholders to allow for more efficient referrals and care management; (2) methods relating to matching the patient with the most appropriate care professionals in the care network platform 200; and (3) methods that leverage the tele-health tools 70 such as, for example, secure chat and messaging tools, video conferencing tools, voice-over internet tools, and file share exchanges, and the data elicitation tools 72 such as, for example, geographic information systems, voice recognition technologies, and facial recognition tools to enhance and automate the care experience and further improve the care matching process. The three subsystems 200, 400, 600 implemented by the systems and components of FIGS. 1A-1C and 2 are discussed in further detail below.

The Care Network Platform/Subsystem

The tele-health care network platform 200 is created by securely linking the patient 52 with one or more healthcare providers 54, non-medical caregivers 56, healthcare advocates 60, family/friends 58, and existing social media networks 62 to form the patient's personal care network 115 (FIG. 2). The care network platform 200 provides a unique social network that enables a marketplace of medical specialists and a unified support experience for the patient 52. As a result, care decisions for complex patient conditions may be addressed in a manner that accounts for an entirety of the patient's care "circle" or team, enabling users to invite others to join the patient's care network 115, invite others to patient visits, share patient data and uploaded content, and be alerted to events related to the patient 52 (new visits, new shares, new group members). Permissions may be set to allow different users in a patient's care network 115 to have appropriately limited insight into the patient's account or complete access, depending on the user. In one embodiment, private care networks may be created within the network platform 200 based on medical group preferences for self-referrals and aimed keeping patients within the respective clinical network.

In use, the collection and sharing of information through the tele-health tools 70 and the data detection and/or elicitation tools 72 available via the user terminals 68 and the tele-health operations center 64 enable medical professionals/providers 54 to efficiently collect, store, and categorize patient data provided from a variety of sources. For example, multiple user terminals 68 interfacing between a variety of stakeholders including multiple healthcare providers 54 enables a unique experience relative to other telemedicine and digital health interfaces, through which the expert care provider simply talks with the patient. The care network platform 200 enables, for example, real-time review of diagnostic data such as laboratory studies and radiographic images on the screen at the terminal 58 operated by the patient 52. The network module 114 may also implement a routing function to route incoming patients 52 appropriately, including prioritization of the queue based on patient profile data, such as the preferred point of contact or any flags added to high-risk individuals.

Moreover, the care network platform 200 may serve as a referral tool to grow a patient's selection of treating healthcare providers 54 and to expose providers 54 to patients 52 on the network platform 200. Adoption of or enrollment in the care network platform 200 may be driven by several means of pushing or pulling a new user (e.g., a patient, a provider, an advocate, etc.) into the ever-expanding care network platform 200. In this regard, the care network module 114 may leverage existing public and private domain social networks 62 and existing directories for physicians and other care providers for identity verification.

In one embodiment, enrolled healthcare providers 54 may invite their trusted peers into the network 200 via online social networks 62 like LinkedIn, Instagram, Facebook, and Snapchat or directly via email. The trusted colleague who is a new user may then offer the care network platform 200 to his or her existing patients for follow up visits or other virtual visits as a new benefit to his or her practice. If an enrolled provider sees a patient 52 on the care network platform 200 and wants to refer the patient 52 to a trusted colleague, the system 200 may access the provider's contacts (e.g., phone contacts, network contacts) and allow for an invitation to be sent (e.g., via a text message or an email initiated via the platform 200) to that trusted colleague to join the network platform 200 in general and the patient's care network 115 specifically to see and treat the patient 52 on the care network platform 200, after having the provider's identity and professional credentials verified. The care network module 114 may also confirm the patient's location and insurance to ensure that the patient 52 is in network with the trusted colleague and then allow the new care provider 54 to bill the patient's insurance after a care interaction.

Figure 3A:
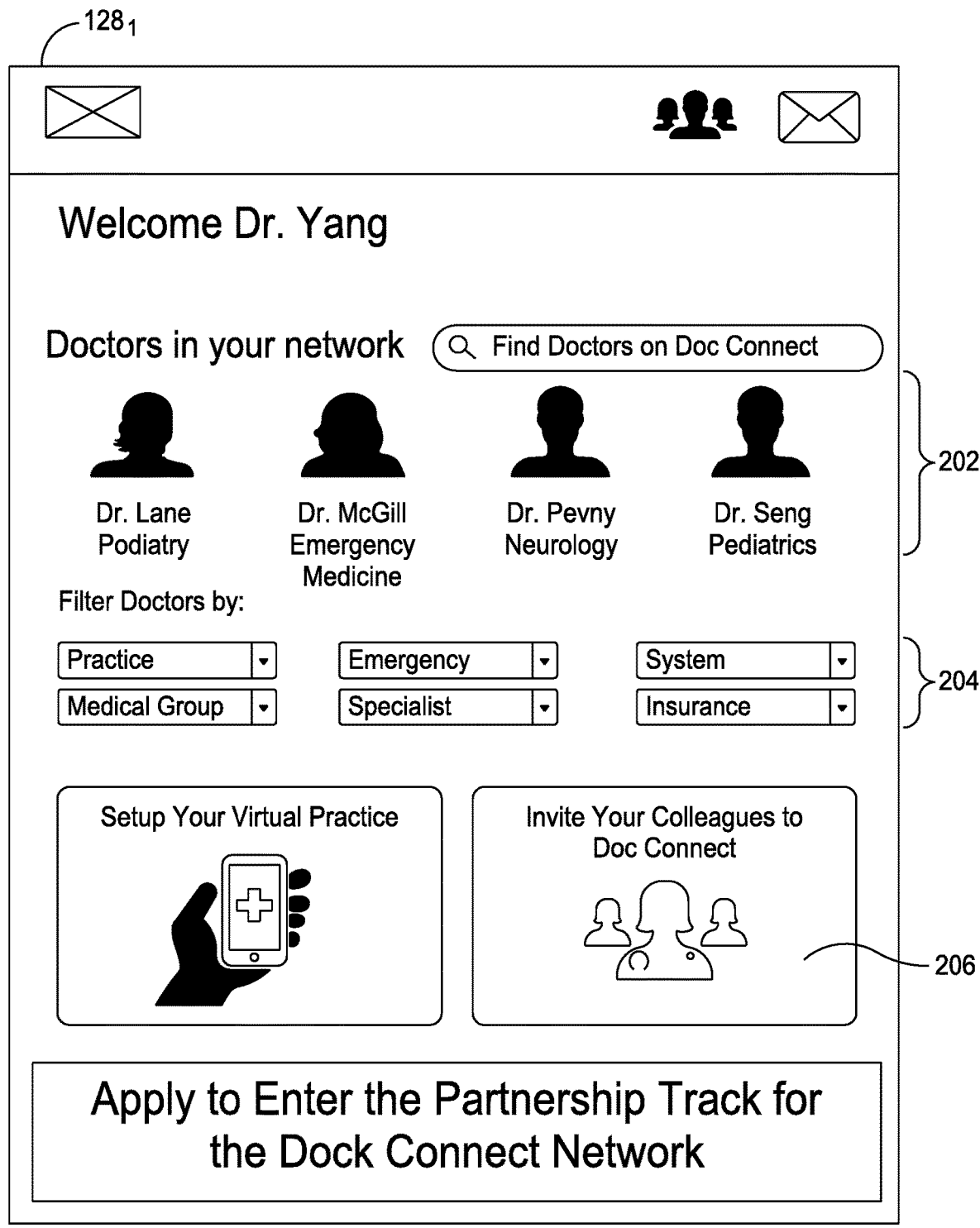
FIGS. 3A-3B illustrate exemplary landing and healthcare provider profile screens, respectively, of a graphical user interface (GUI) for display on various user terminals during an operational workflow of the systems of FIGS. 1A-1C.

FIG. 3A illustrates an exemplary landing page or screen $128_1$ for an enrolled healthcare provider 54, which presents a number of items of information and options including a listing of the other providers in the provider's network 202, filtering options 204, and an invitation link 206 to invite additional respected colleagues into the care network platform 200.

Figure 3B:
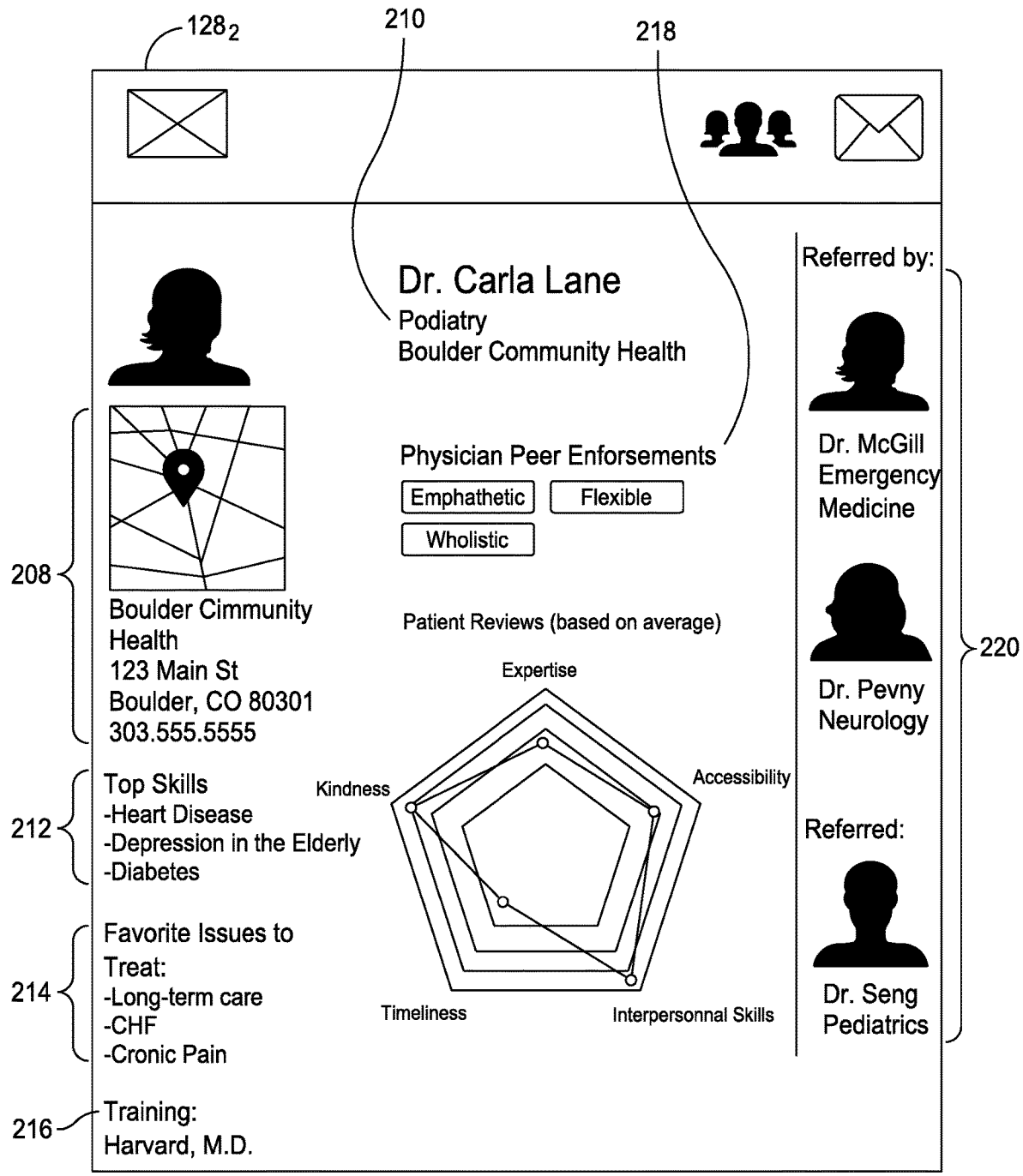

FIG. 3B illustrates an exemplary healthcare provider profile page or screen $128_2$ that may be available for viewing/referring via the care network platform 200. As shown, the profile page $128_2$ may present the provider's location 208, specialty 210, professional experience 212, interests 214, professional training 216, peer-to-peer ratings 218, and peer review/referral 220, if available. Embodiments of the preconfigured and interactive screens or pages $128_{1-n}$ implemented via the GUI module 110 as part of the GUI 126 may have any appropriate look or feel and may contain any appropriate and/or desired content.

Figure 4:
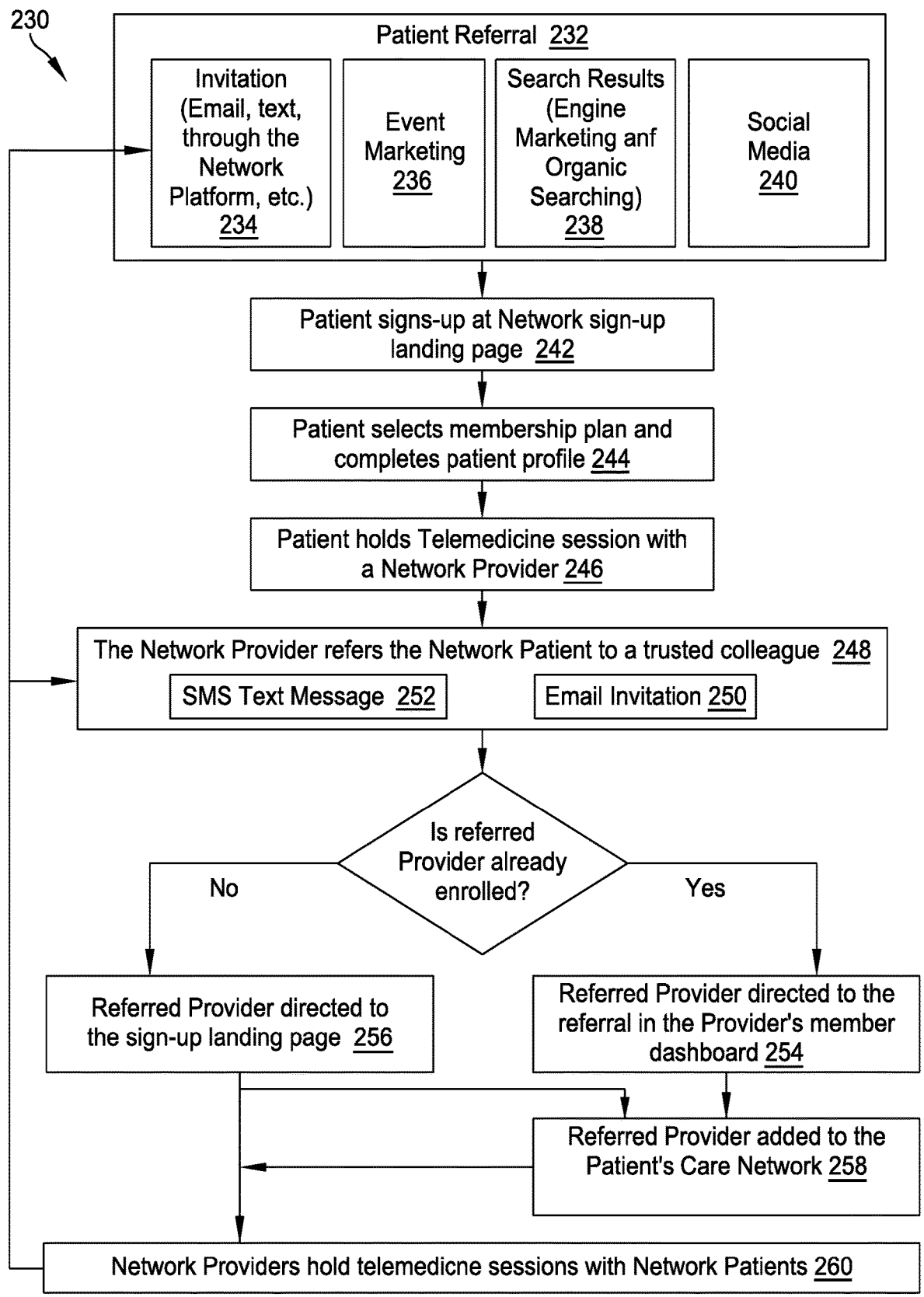
FIG. 4 provides a flowchart depicting an exemplary workflow for a referral and tele-medicine use process of the care network subsystem of FIG. 1A.

FIG. 4 provides a flowchart depicting an exemplary workflow for a referral and tele-medicine use process (FIG. 4, 230) of the growing care network platform 200, in which a patient 52 may be referred, join the care network platform 200, hold telemedicine sessions with one or more enrolled network providers 54 in the patient's growing care network 115, and where a provider 54 may be similarly referred, join the care network platform 200, be added to the patient's particular care network 115, hold telemedicine sessions with the patient 52, receive patient feedback, invite other colleagues to the larger network platform 200 and/or the patient's care network 115 therein, and to invite other non-medical invitees into the network platform 200 and the patient's care network 115.

The process (230) may begin with a patient referral (232) to the platform 200 via one or more referral sources such as, for example, an invitation initiated via the network platform 200 (234), via event marketing (236), via computerized search results (238) referring the user to the platform 200, and/or via a social media platform 62 (240). Once the referred patient 52 has navigated to the care network platform 200 via the user terminal 68, the user may enroll in the care network platform 200 via a sign-up landing screen (242) and complete a membership profile, including selecting a membership plan (244). After the patient 52 has enrolled, the patient 52 may hold a telemedicine session or interaction with an enrolled network provider 54 (246), who becomes part of the patient's patient care network 115. The provider 54 may then refer the patient 52 to a trusted colleague (248) via, for example, an email invitation (250) or a text invitation (FIG. 4, 252) initiated via the platform 200. If the referred provider is already enrolled, the provider 54 may be directed directly to a member dashboard page for the provider 54 (254), where the provider 54 may be added to the patient's care network 115 (258). If the referred provider is not already enrolled, the referred provider may be directed to a sign-up or enrollment landing page (256) before being added to the patient's care network 114 (258). Once enrolled and incorporated into one or more patients' care network(s) 115, the enrolled network providers 54 may hold telemedicine sessions with the enrolled network patients 52 (260), and as a result of the ongoing patient-provider interactions, additional referrals/invitations may be sent to additional patients and/or providers to organically grow enrollment in the care network platform 200.

Figure 5:
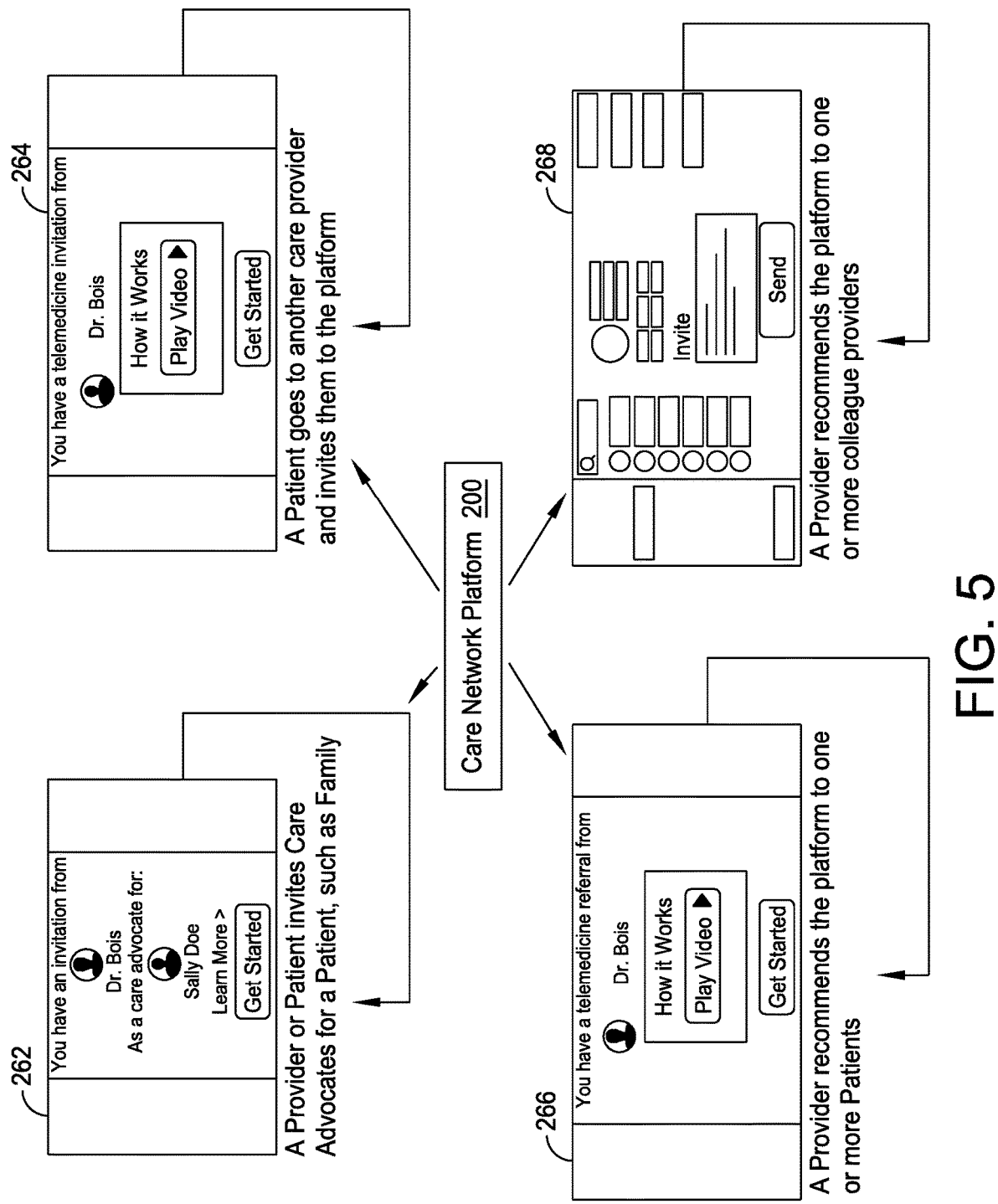
FIG. 5 provides a functional schematic depicting a plurality of continual growth models for the care network platform of FIG. 1A.

FIG. 5 provides a schematic depicting a plurality of continual growth models for the care network platform 200. In one model, an enrolled healthcare provider 54 or patient 52 may invite one or more care advocates for the patient 52, such as, for example, one or more family members or friends 58, or may invite one or more caregivers 56 (262) to join the platform 200 and the patient's care network 115. These stakeholders may enroll in the platform 200 and join the patient's care network 115 in a manner similar to that discussed above in relation to FIG. 4. In another model, the patient 52 may visit another healthcare provider 52 and invite provider into the platform 200 (264). An enrolled healthcare provider 54 may also recommend and invite one or more patients into the platform 200 (266) and/or one or more colleagues into the platform 200 (268). Through the growth models depicted in FIGS. 4-5, the care network platform 200 may grow organically through invitations provided from and to any of the user types—the patients 52, the healthcare providers 54, the caregivers 56, the family/friends 58, and/or the healthcare advocates 60.

Figure 6:
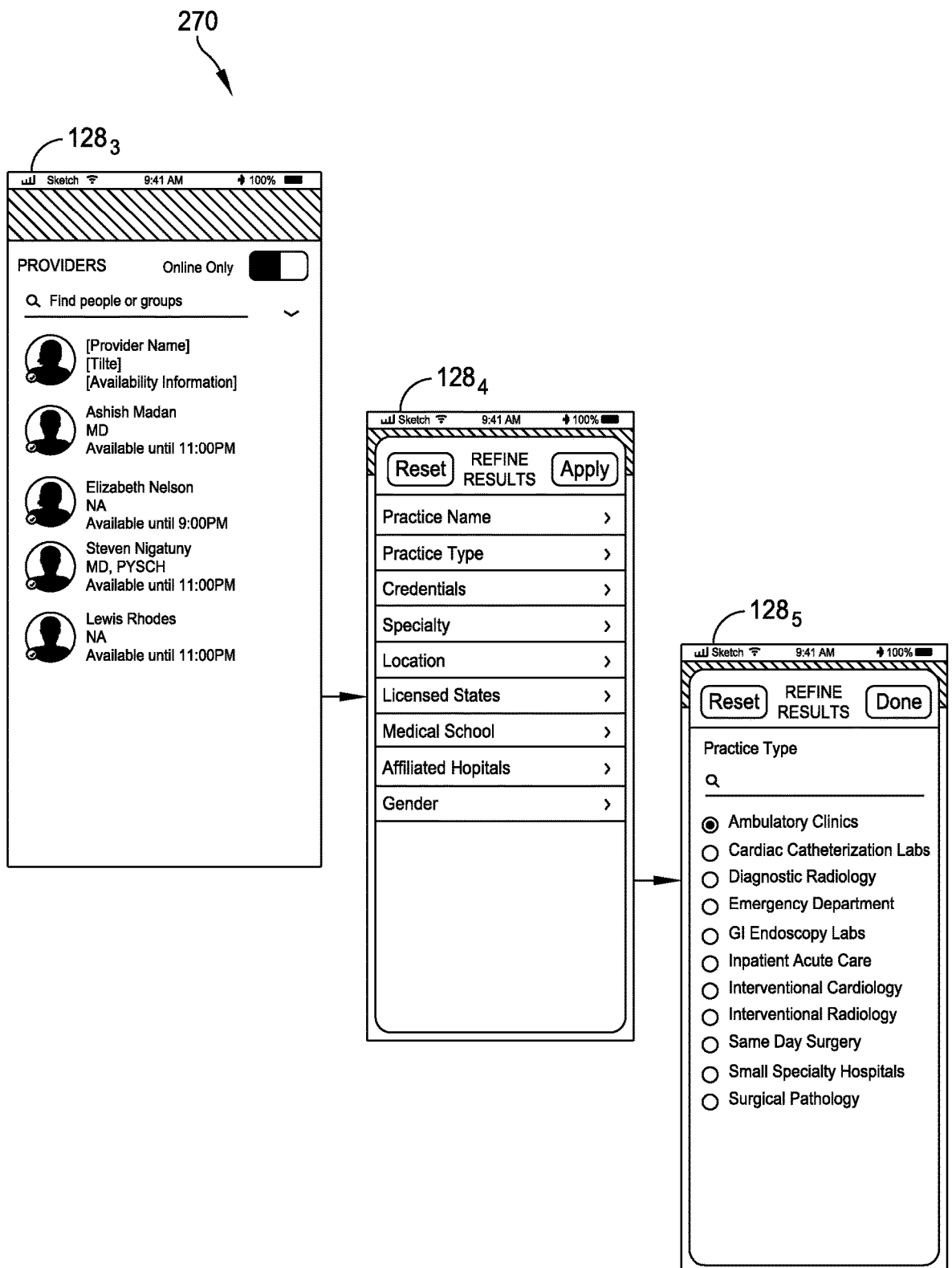
FIG. 6 provides a plurality of expanded, preconfigured and interactive GUI screens displaying a functionality of a care network directory of the care network subsystem of FIG. 1A.
Figure 7:
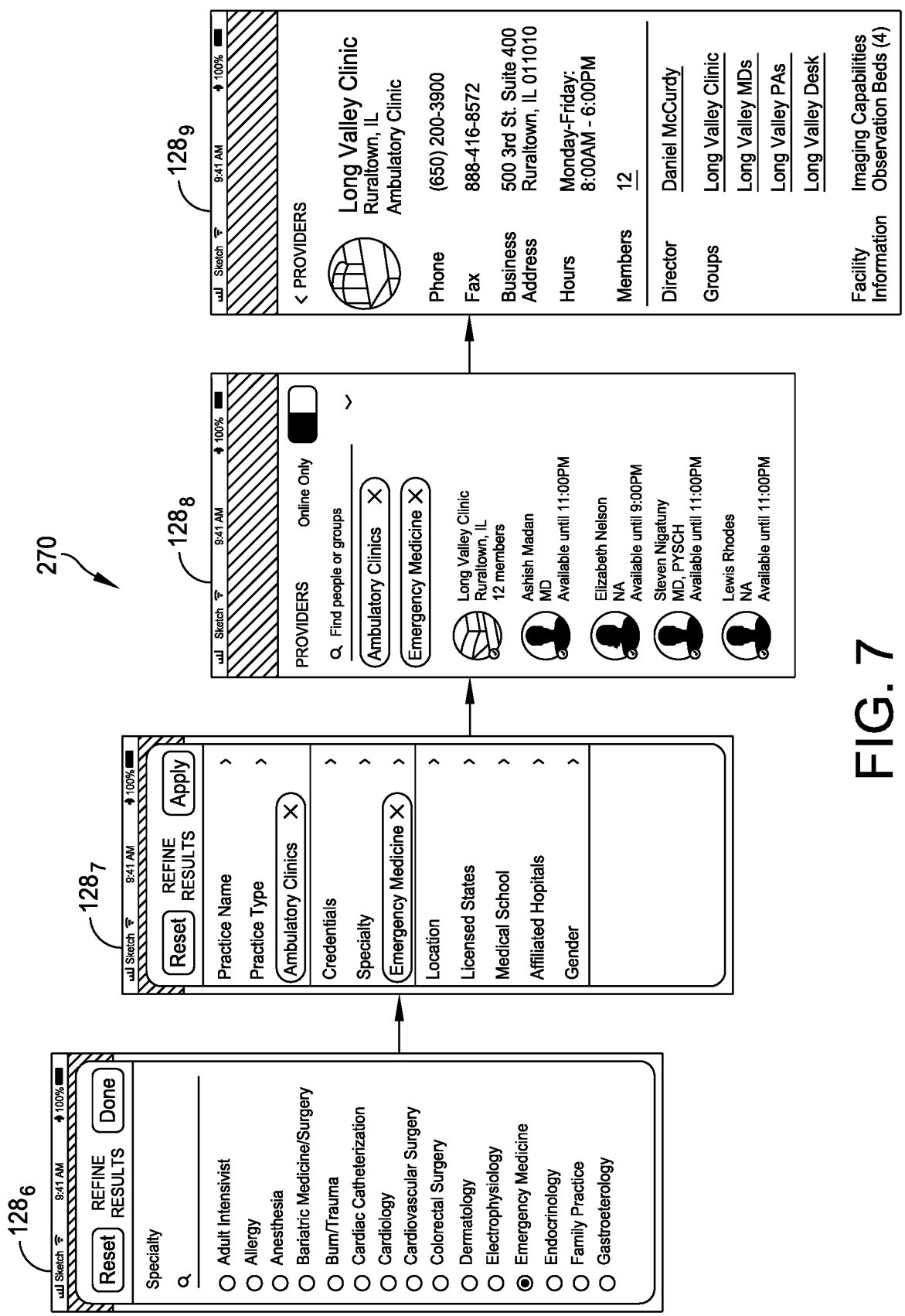
FIG. 7 provides a plurality of additional expanded, preconfigured and interactive GUI screens displaying the functionality of a care network directory of the care network subsystem of FIG. 1A.

FIGS. 6-7 illustrate an exemplary expanded care network directory 270 for enrolled healthcare providers 54, including a provider directory screen $128_3$ presenting provider accessibility information, such as the hours the provider is on call, whether the provider is currently online using the application. As shown in FIG. 6, the provider directory screen $128_3$ may expand to a provider filter screen $128_4$ that presents a number of filter categories that allow the filtering of results by a combination of categories, including practice type as shown in a practice-type filter screen $128_5$, as well as practice name, location, specialty, credentials, medical school, affiliated hospitals, and licensed states. Within each category, further filtering options may be provided to provide access to any appropriate type and/or desired provider information.

As shown in FIG. 7, the exemplary care network directory 270 may be further expanded with an applied provider specialty filter to a provider specialty selection screen $128_6$ and a refine results screen $128_7$, then to a results screen $128_8$ displaying providers specializing in ambulatory clinics and emergency medicine, and finally to results screen $128_9$ displaying contact and hours information in addition to other desired fields such as, for example, the practice's director, for a selected enrolled provider 54.

Figure 8:
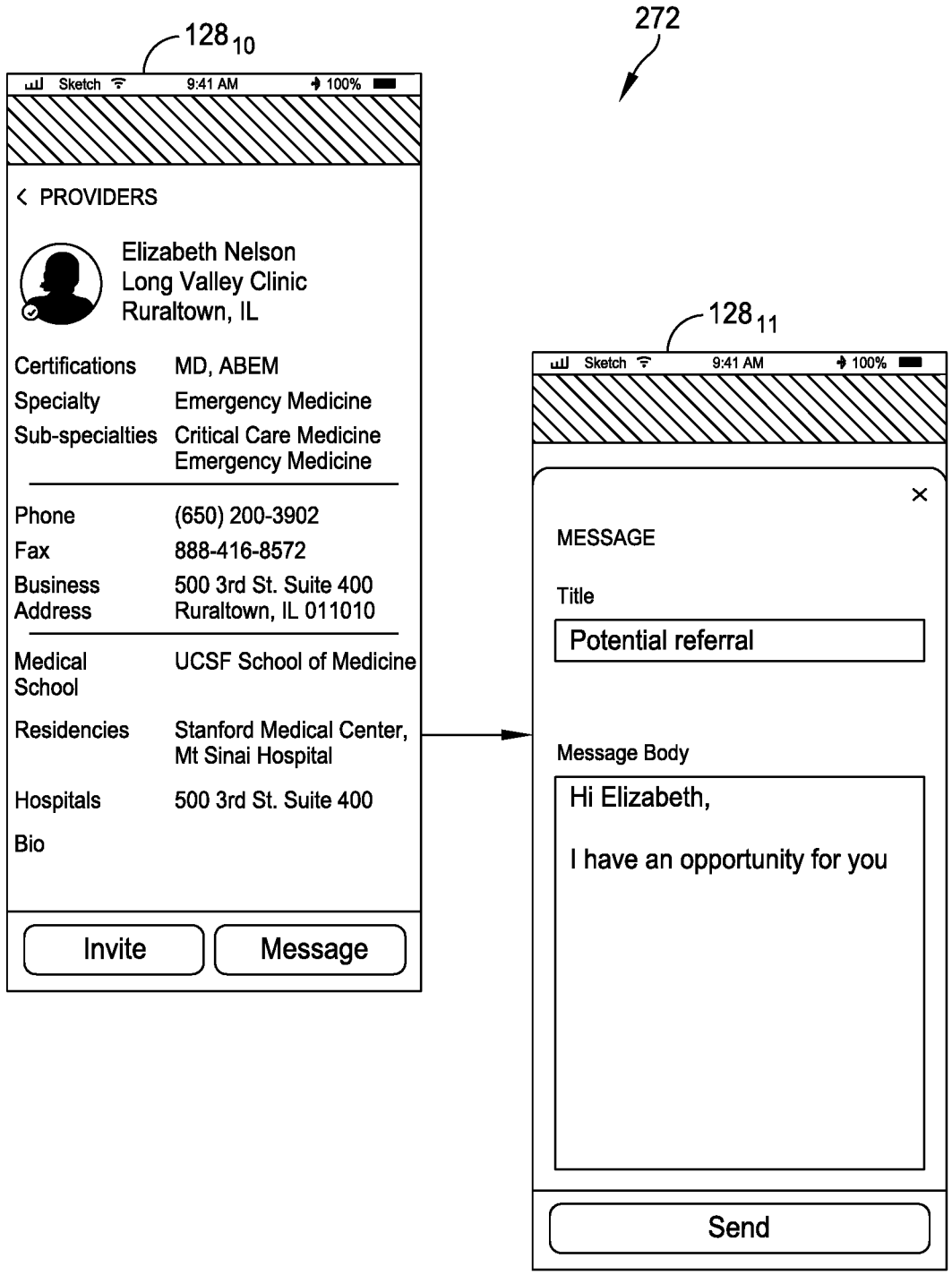
FIG. 8 provides a plurality of expanded, preconfigured and interactive GUI screens displaying a functionality of an integrated messaging tool of the care network directory of the care network subsystem of FIG. 1A.
Figure 9:
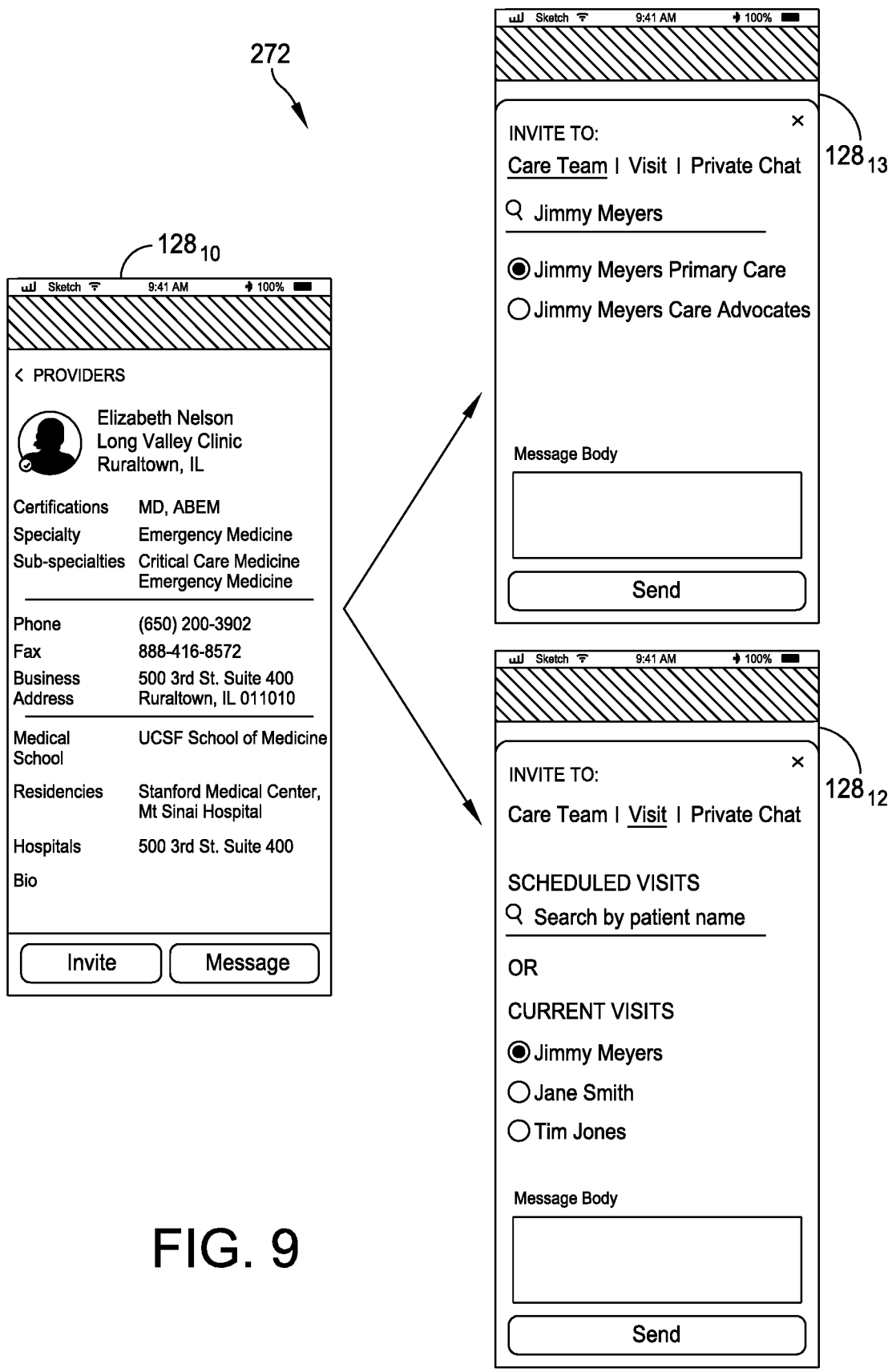
FIG. 9 provides a plurality of additional expanded, preconfigured and interactive GUI screens displaying the functionality of the messaging tool of the care network subsystem of FIG. 1A.

FIG. 8 illustrates one embodiment of an integrated messaging tool (e.g., email and/or text messaging capabilities) 272. In operation and in one embodiment, the messaging tool 272 may be integrated into a provider's profile page $128_{10}$ for use in communicating with other providers 54 enrolled in the care network platform 200, as shown in an expanded messaging screen $128_{11}$. Using embodiments of the integrated messaging tool 272, healthcare providers 54 may communicate with one another and/or with other stakeholders enrolled in the platform 200. For example, as shown in FIG. 9, in addition to private chats or messaging, the messaging tool 272 allows providers to be invited directly to patient visits and/or participate in care team communications with patients or other providers, advocates, and/or friends and family in the patient's care network, as shown in invitation screens $128_{12}$ and $128_{13}$, respectively.

The care network platform 200 provides a number of benefits over the ways in which tele-health services are currently provided. Initially, there are lower barriers to network entry than on existing platforms. Currently, tele-health technologies are sold for a price to practitioners/providers and to patients via out of pocket expenses or a copay. The majority of tele-health services to date have not been integrated with local care by established physicians/providers for a more engaged relationship between patients and providers enabled with virtual care tools. Both of these issues have created friction impacting the disseminated adoption of a universal tele-health platform. The care network platform 200 helps connect patients and providers for free. Providers may then bill for tele-health services in many clinical scenarios, benefiting their practice at zero cost to enter the technology.

The care network 200 provides for cross-practice collaboration. Further value is created for providers enrolled in the platform 200 by being able to interconnect and communicate with other providers 54 on the platform, allowing for more efficient referrals and care management.

In one embodiment, users may promote the platform on social media tools for unlocking additional care network communication features to further spread awareness of the platform 200 to help expand the care network. In this regard, the care network platform 200 also provides broader inclusivity. The participation of healthcare professionals 54 and non-professional caregivers 56, care advocates 60, family members and friends 58, and other stakeholders, as well as enabling network access to social media platforms 62 assists in care communication on behalf of the patient 52, especially for the patient 52 with a complex, chronic disease or complicated social determinants of health. Inclusion of a patient's full social network/circle makes the care network platform 200 different. Existing systems connect healthcare professionals to patients but fail to include the full range of caregivers, including friends, family and personal healthcare advocates.

The care network platform 200 provides for secure, multi-modal communications. By allowing free access to this HIPAA-compliant, medical-grade communication tool, real-time seamless communication in a care community can take place without large amounts of overhead or health system-level administration. Providers, non-professional caregivers, and patients can also intercommunicate to coordinate care using live video, secure messaging, and secure phone lines with an ongoing electronic medical record of interactions and key medical information.

Embodiments of the care network platform 200 provide support for concierge roles and care coordinators. In one embodiment, a user or users may be designated as a "Care QB," which is a special designation given to specific users of the system to ensure every practice can deliver consistent, predictable experiences for their patients. The Care QB acts as the primary and default point of contact for the patient in the healthcare practice and may differ based on the patient. The Care QB may also be tasked with assembling the patient's Care Network 115, by inviting other practitioners. Depending on the need, the Care QB role also may provide concierge services for the patient such as placing orders, assisting with transportation, or connecting with outside specialists, all through the care network.

The care network platform 200 also supports multiple types of provider relationships. Embodiments of the care network platform 200 employ a provider ownership joint-venture model, thereby enabling smaller independent practices to test new service offerings and develop tele-medicine competencies with less risk. The provider relationship to tele-health solutions typically uses one of two models: an employment contractor model or an "Uber" joint venture model. With the care network platform 200, a direct partnership between the healthcare providers 54 as joint venturers with the technology company allows for deeper alignment of end points for the service. By leveraging local care providers relationships and know-how via the care network platform 200, better population health services may be offered to payers to outcompete existing offerings in a local healthcare market, and by giving providers an upside in a joint venture they are more incentivized to participate in the care network platform 200.

The care network platform 200 is also applicable other professional service industries beyond healthcare where care and compassion play a role engaging customers, users or clients, like education, financial services, non-profits and faith-based organizations.

Care Match Platform/Subsystem

Notably, most existing methodologies for matching patients with healthcare providers use simple star ratings for the healthcare providers, followed by patients choosing a provider. However, patient satisfaction scores are a failed tool for optimizing natural compassion and care from a human being. While there are healthcare providers that consistently provide excellent patient satisfaction based on universal, aggregated survey data, many or most care professionals only provide average care and compassion. While patients can be directed to care providers based on their training and expertise fitting their specific medical problem, it is currently impossible to allow for patients and providers to be matched up based on prior patterns of care interactions.

The care match subsystem or platform 400 matches patients 52 and providers 54 based on ratings as well as matched "personas" between patients 52 and providers 54, such that patient satisfaction can be improved on an aggregate level when personality traits and interests are better matched. Embodiments of the care match subsystem 400 and the care match module 116 may implement two complimentary tools that assist in matching patients with their optimal healthcare providers for both tele-health and in-person interactions: a personality assessment tool or tools and a ratings and reputation system implemented by the personality assessment module 120 and the ratings and reputations module 118 of the care match module 116 of FIG. 2, respectively.

Figure 10:
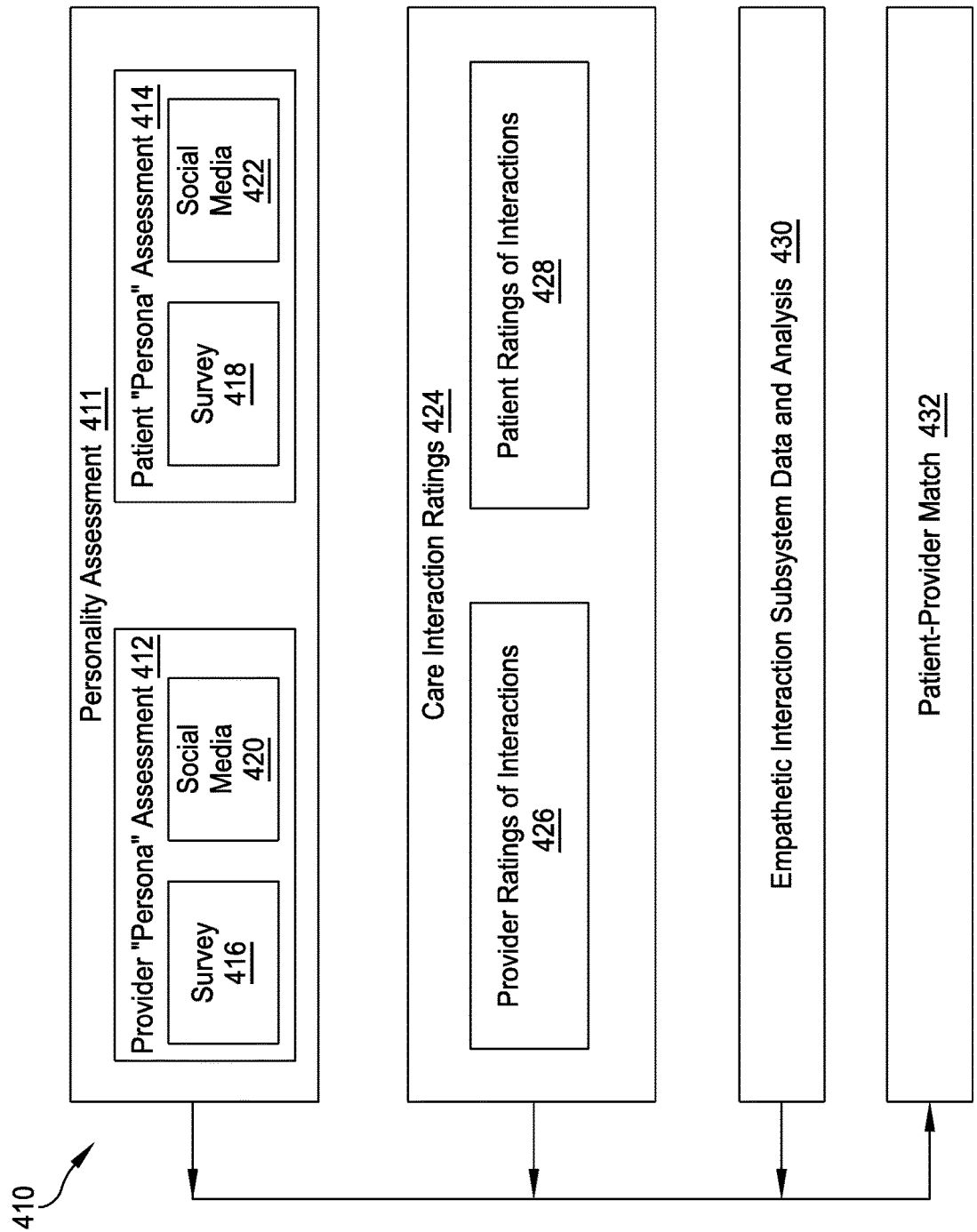
FIG. 10 provides a flowchart detailing an exemplary method of matching enrolled patients and providers using the care match subsystem of FIG. 1A.

FIG. 10 provides a flowchart detailing an exemplary method of matching enrolled patients 52 and providers 54 (410) based on personality assessment or "persona" together with provider ratings and reputation developed through the provider's prior patterns of care interactions. In one embodiment, a personality assessment (411) may be provided or taken by both patients 52 (412) and healthcare providers 54 (414), as implemented via the personality assessment module 114 (FIG. 2) including a series of simple survey questions (416, 418) to better identify their personality type and their interpersonal communication style(s), or the patients 52 and providers 54 may rate or "tune" preferences along differential scales. From these assessments, the system may create confidential and categorical "personas." In one embodiment, the personality assessment (411) may involve both the patient 52 and the provider 54 generating a structured mini-biography of who they are as a person, as well as who they are as a patient or a provider, to facilitate more meaningful connections between the patient 52 and the provider 54. The mini-biography format may be incorporated into the standard EMR-agnostic intake form, into the care matching platform 400 through which the various providers 54 and medical groups interface with the patient 52, and/or into existing medical group/patient interface platforms already in place. The ability to retrieve data from other social media platforms via the care network platform 200 (420, 422), as discussed above, enables further profile or persona building, and further aids matches between care providers and patients.

In addition, actual care interactions (e.g., both virtual and in person) between patients 52 and healthcare providers 54 may be measured using retrospective ratings (424) provided by patients and providers (426, 428) to help grade the level of care a patient felt from the care interaction. That is, the ratings and reputation module 118 (FIG. 2) may implement a survey or other rating mechanism in which the patients 52 may rate the quality of care they felt they received from a healthcare provider 54 using a method based on semantic differential scales (428), and providers 54 may similarly rate the quality of care they felt they provided or that they perceived the patient 52 to have received (426). The confidential, undisclosed ratings may then be used to determine if specific and known personality types and/or communication styles (e.g., learned/known from the personality assessment (412)) or clinical scenarios lend themselves to a positive or negative interaction to help guide future recommendations to patients 52 regarding who they should seek out for care based on their personality type, communication style, and/or clinical problem.

Similarly, real-time recorded interaction data and emotional reaction information and sentiment analysis extracted from actual patient-provider interactions and outcomes gathered via the empathetic interaction subsystem 600, as discussed below in relation to FIGS. 12-17, may provide an additional input (430) to improve an ultimate patient-provider care match (432) provided by the care match subsystem 400, such that the match is a function of one or more of the personality assessment (412), the post-care interaction ratings (424), and the real-time empathetic interaction subsystem data and analysis (430).

By comparing patient and provider "personas" from the personality assessment (412), along with interaction care ratings (424) and real-time emotion data and sentiment analysis (430) from the empathetic interaction subsystem 600, the care match subsystem 400 and the care match software module 116 employ a learning algorithm that identifies common patterns that enable selection of care providers for patients (432) that will most likely make patients 52 feel most cared for.

Figure 11:
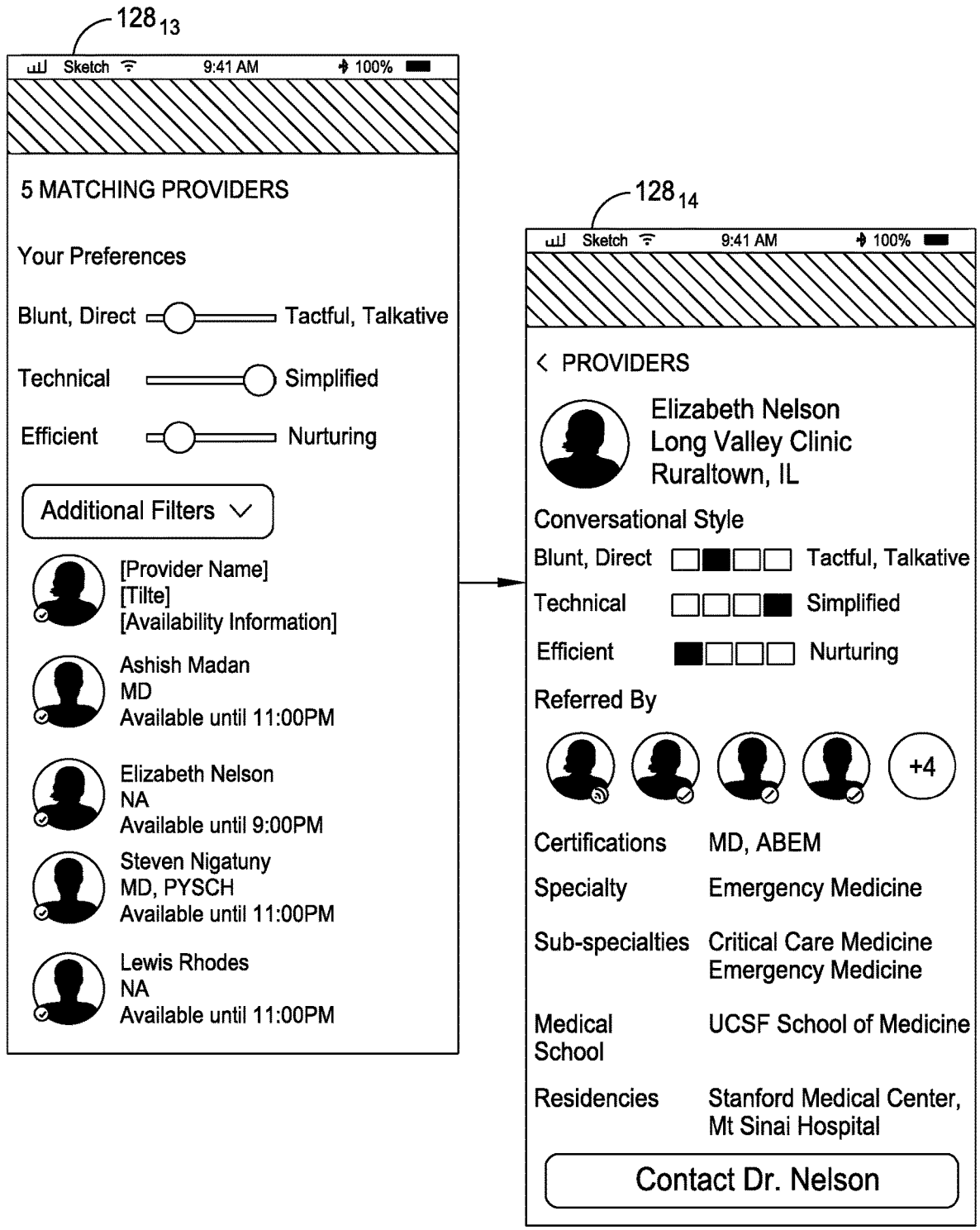
FIG. 11 provides a plurality of expanded, preconfigured and interactive GUI screens displaying a functionality of the care match subsystem of FIG. 1A.

In one embodiment, in addition to performing quality assurance and review of care interactions (424) provided through the care network platform 200, patients may opt to have a provider recommended to them based on the best fit with their communication style and personality to achieve an optimal care match (432). FIG. 11 illustrates an exemplary recommendations screen $128_{13}$ for display via the terminal 68 operated by the patient 52 regarding the recommended care professionals, or provider matches, that would be the best fit for the patient. From the recommended providers 54, patients may view a core provider information screen $128_{14}$ for each of the matched providers, which may display, for example, other users who referred the provider in the past and a summary of how well the physician's persona matches the patient's target attributes.

Empathetic Interactions Platform/Subsystem

Healthcare professionals are currently inundated with non-clinical tasks and have to use antiquated technology that keeps them from easily engaging in the clinical care experience. The healthcare industry ranks as the least favorable industry by American consumers today, relative to any other industry in America. Additionally, over 50% of physicians voice feeling burnt out in the modern day practice of medicine. Real-time feedback on a care interaction or experience is currently not possible, meaning that it is also not possible for today's clinicians to learn how they are being perceived by patients within a meaningful time frame, if at all. If there is a poor care interaction, feedback may not reach the clinician for two weeks, two months, or not at all. This issue also applies between clinicians and other care team members, making it more difficult to foster an empathetic culture between clinicians and support staff.

The empathetic interactions subsystem 600, operating in conjunction with the care network platform 200 and the care match subsystem 400, employs emotion and sentiment analysis of actual patient-provider interactions and outcomes to optimize the patient experience, ensure the patient feels cared for, and provide a feedback loop to improve and/or automate the care match process and analysis discussed above. Emotional responses may be measured by the data elicitation tools 72 (FIG. 1B) such as geographic information systems, facial expression recognition, and voice intonation recognition technologies to help determine whether an in-person or tele-health/virtual care interaction or experience yielded/is yielding a positive emotional response from both the provider 54 and the patient 52. The empathetic interactions subsystem 600 may also be applied to ensure a better connection between care team members to ensure a healthy, empathetic culture between clinicians and support staff.

In one exemplary embodiment, facial expression recognition may involve recognition of a sad face versus a happy face. These measurements may then be correlated with patient engagement and compliance with treatments for driving positive health outcomes. Embodiments of the empathetic interactions subsystem 600 may also implement an "empathy meter" 602, as displayed via an exemplary empathy meter screen $128_{15}$ of FIG. 13, which acts as a screening tool for healthcare providers 54 to see in real time if a patient is feeling cared for or, more importantly, not cared for, based on a machine learning algorithm of the empathetic interaction module 122 (FIG. 2), which has been trained to identify linguistic, visual, and other markers indicating different emotional states, including, for example, happiness, sadness, frustration, fear, disgust, joy, anger, humor, anxiety, and so on.

Figure 12:
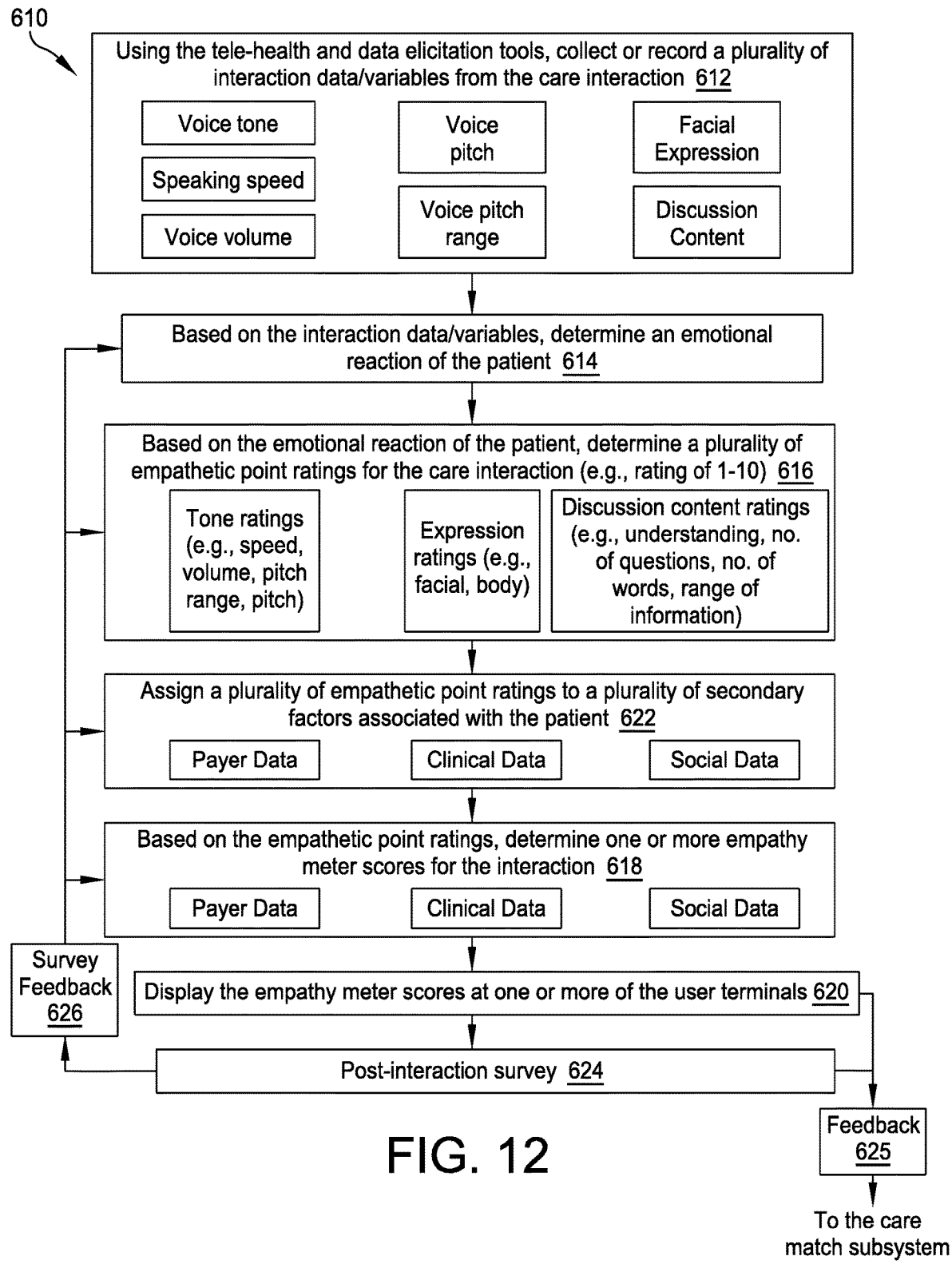
FIG. 12 provides a flowchart depicting one embodiment of a method of evaluating or ranking an emotional response to a care interaction between a patient and a healthcare provider using the empathetic interactions subsystem of FIG. 1A.
Figure 13:
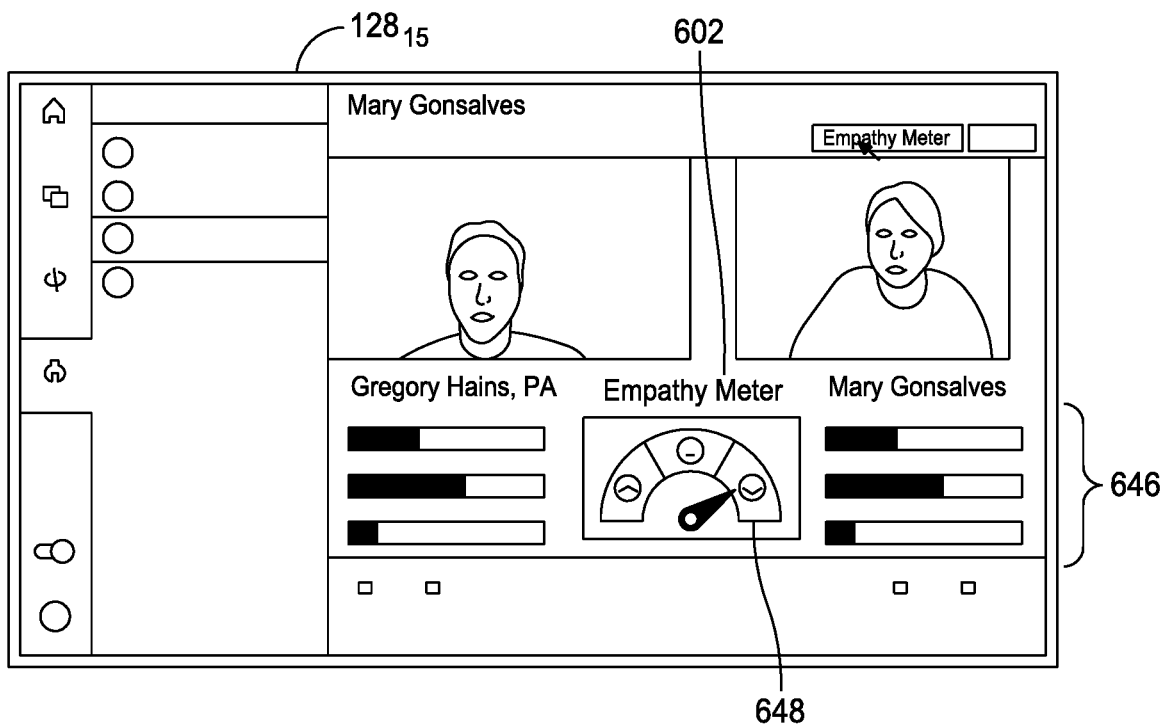
FIG. 13 provides an exemplary, preconfigured and interactive empathy meter GUI screen reflecting a plurality of empathy meter scores for a care interaction analyzed using the empathetic interactions subsystem of FIG. 1A.
Figure 14:
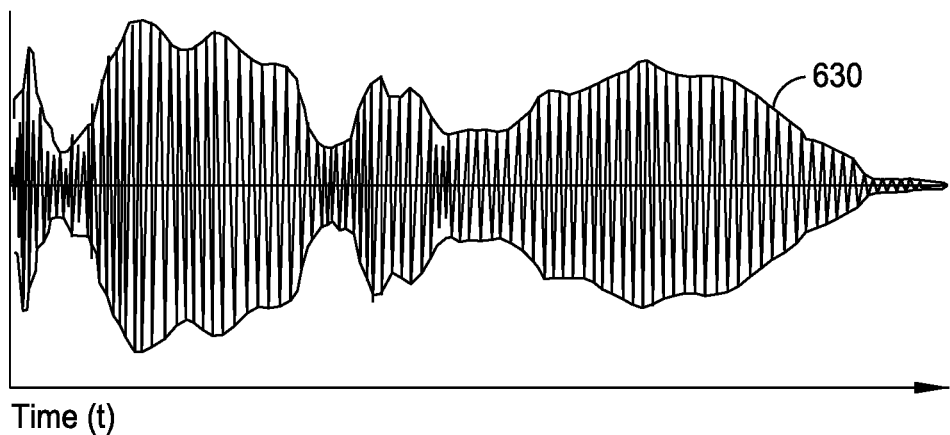
FIG. 14 depicts an exemplary record of a sound wave envelope of a human voice.

FIG. 12 provides a flowchart depicting one embodiment of a method of evaluating or ranking an emotional response to a care interaction between a patient 52 and a healthcare provider 54 (610). In one embodiment, the patients 52 and the providers 54 may consent to allow the tele-health tools 70 and the associated data detection and/or elicitation tools 72 present on the user terminal 68 (e.g., smartphone terminal, desktop terminal, other mobile device) or an associated device (e.g., sensor technology present in patient or examination rooms) to listen to and watch their in-person or virtual care interaction (either a virtual interaction or a real-life interaction) and record emotional cues, or interaction data/variables 640 for storage in the interaction database 88, indicating whether or not an interaction is being perceived as compassionate and caring (FIG. 12, 612). That is, through the data detection/elicitation tools and sensors 72 such as geographic information systems (GISs), voice recognition tools, and facial recognition tools, the empathetic interaction module 122 of the networking, care matching, and empathetic interaction software 100 of FIG. 2 may collect the objective recorded interaction data/variables 640 reflecting the emotional tones of conversations, verbiage of conversations, facial expressions, body language, posture (e.g., collect a photograph of a facial expression or body position captured during the care interaction, record an audio transcript of the care interaction, record a video of care interaction), and other emotional indicators (FIG. 12, 612), and employ a machine learning algorithm of the empathetic interaction module 122 to assess the recorded interaction data/variables 640 and determine and store corresponding emotional reaction information 642 in the interaction database 88, which reflects an emotional reaction, state, and/or change of state of the patient 52 (FIG. 12, 614).

For example, the empathetic interaction subsystem 600 may determine the emotional reaction information 642 associated with the recorded interaction data/variables 640 in real time during the interaction. The emotional reaction information 642 may reflect, for example, whether the patient 52 is feeling at ease, feeling comforted, enjoying the interaction, or conversely, whether the patient 52 is feeling frustrated, confused, scared, or disappointed relative to how he or she felt prior to the beginning of the interaction. In further detail, and in conjunction with the data detection/elicitation tools 72 and the tele-health tools 70 employed at the patient and/or provider terminals 68 and employing machine learning techniques, the empathetic interaction module 122 may determine, in real time, whether the patient 52 and/or the provider 54 is or is not feeling cared for or is or is not feeling an empathetic connection during the care interaction (e.g., determine whether a recorded expression represents a sad or a happy face).

To provide an example, FIGS. 14 and 15A-15C provide recorded interaction data in the form of a sound wave envelope 630 and associated statistical charts 632, 634, 636, respectively, which may be used to interpret the sound wave envelope 630 into emotional reaction information. The intonation charts 632, 634, 636 of FIGS. 15A-15C reflect initial voice intonation baselines, with changes in voice intonation that statistically suggest different emotional states associated with known intonation responses. Specifically, the intonation chart 632 of FIG. 15A reflects vocal statistics obtained from recorded speech samples for a normal emotional state, while the intonation charts 634 and 636 of FIGS. 15B and 15C reflect vocal statics obtained from recorded speech samples for angry and panicked emotional states, respectively. This type of statistical data may be compared to the patient's and/or the provider's collected or recorded interaction data/variables 640 and used to determine the patient's and/or the provider's emotional reaction information 642, or their emotional reaction or experience during the care interaction (FIG. 12, 614), based on a voice recording of the care interaction. Notably, baseline initial facial recognition, with changes in facial expression and angles of the face to suggest emotional states and responses, may be similarly charted along with a variety of other correlations between physical responses and emotional reactions or states (e.g., fidgeting suggesting anxiety, slouched posture suggesting disinterest, gesticulating hands suggesting exasperation).

In this regard, the empathetic interaction module 122 of the networking, care matching, and empathetic interaction software 100 may consider a variety of variables or categories of recorded or measured interaction data/variables 640 throughout a care session or interaction. By way of limited example, the following measured or recorded interaction data/variables 640 may be analyzed by the empathetic interaction module 122 for determining an emotional state or reaction of both the patient 52 and the provider 54: (1) Voice, including voice tone, pitch, pitch range, speed, volume, and intonation for determining a correlating emotional state; (2) Facial expression for determining whether the clinician and/or patient is happy or sad, calm or anxious, angry, laughing or crying, catatonic or expressive, and so on; (3) Body language for determining a correlating emotion state; (4) Posture for determining a correlating emotional state; and (5) Discussion content for determining whether the clinician's or the patient's words are detailed, abrupt, courteous, and/or factual.

A variety of emotional reaction information 642 may be gleaned from the recorded interaction variables 640 and may include, for example: (1) Emotional reaction information 642 based on voice-related recorded variables such as frustration, anxiety, or excitement; (2) Emotional reaction information 642 based upon facial expression and/or body language information such as friendliness, variability in expression, anger, sadness, humor/laughter, and happiness; and (3) Emotional reaction information 642 based on discussion content, including whether key phrases were stated or not stated, comprehensive content quality, an amount of questions, an amount of statements, a courteousness level, and/or an interest level.

The recorded interaction data/variables 640 and the resulting emotional reaction information 642 may be used to rate various aspects of the care experience or interaction, as well as the care experience as a whole, on an empathetic point rating system (e.g., a 10 point rating system in which 1 is the least empathetic and 10 is the most empathetic) defined by or based upon a plurality of predefined empathetic criteria such as, for example, tone, expression, and discussion content (FIG. 12, 616). Such empathetic point ratings 644 may be stored in the interaction database 88 and assigned to the emotional reaction information 642, which may, in turn, be applied by the neural network module 124 to implement a neural decision-making network, such as the exemplary neural network 638 shown in FIGS. 16A-16C, to interpret the emotional reaction information 642 and associated empathetic point ratings 644 and determine an ultimate "empathy meter" score or scores 646 reflecting whether or not the patient feels/felt cared for during the care interaction (FIG. 12, 618), which may then be displayed upon the empathy meter screen $128_{15}$ of FIG. 13 at any one of the user terminals 68 (FIG. 12, 620). In this embodiment, the empathy meter screen $128_{15}$ may display empathy meter scores 646 for both the provider 54 and the patient 52 relating to tone, expression, and content, as well as a comprehensive empathy meter score depicted as a comprehensive meter graphic 648 for the care interaction (e.g., green smile, yellow flat mouth, or red frown). Embodiments of the empathy meter display screen $128_{15}$ may take any appropriate format and include any appropriate empathy meter score or scores 646 for the relevant stakeholders to the care interaction.

Figure 16A:
Figure 17:
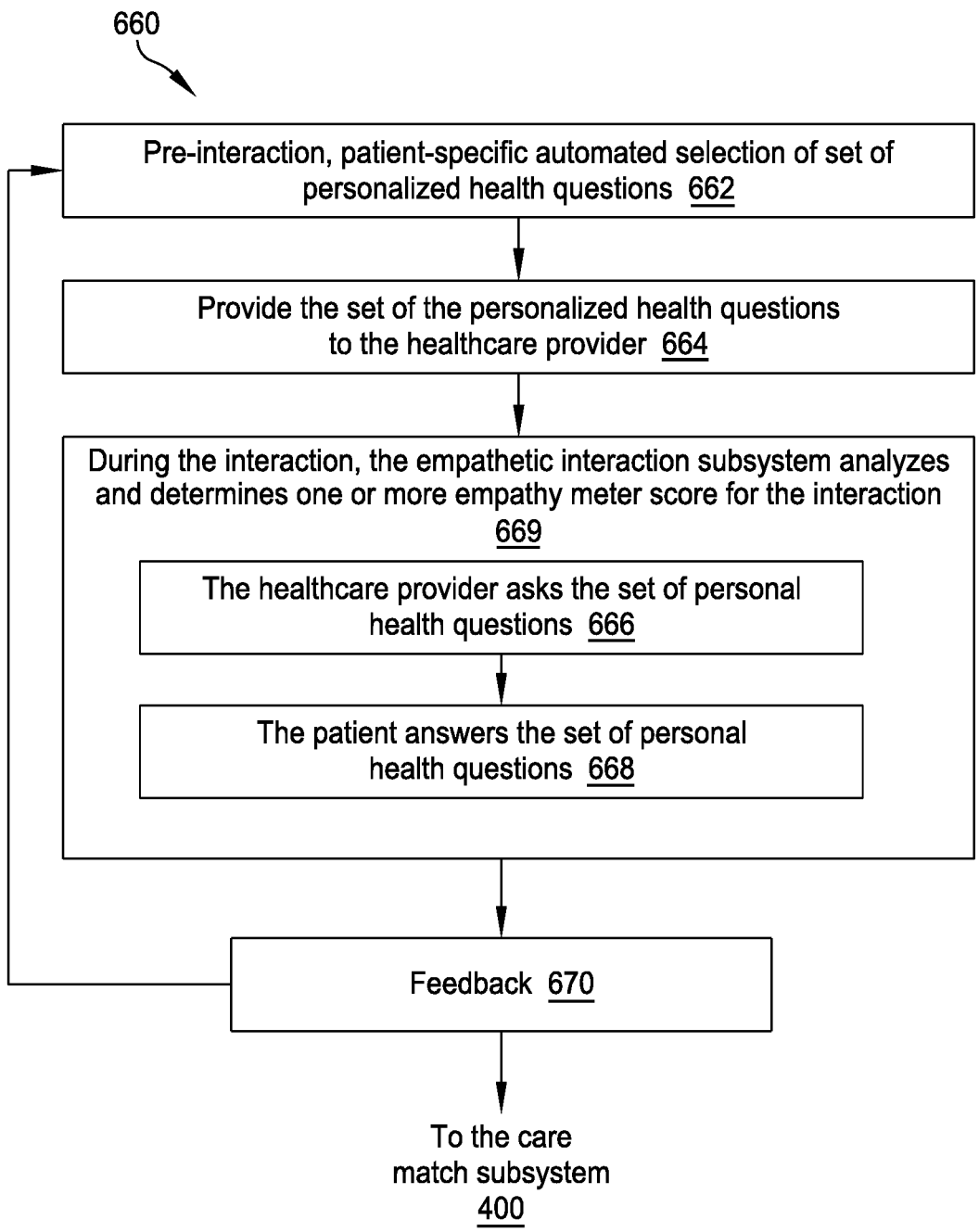
FIG. 17 provides a flowchart depicting an exemplary improved method of patient care facilitated by the empathetic interactions subsystem of FIG. 1.

In addition and as shown in FIGS. 16A-16B, embodiments of the empathetic interaction module 122 and the neural network 638 may also account for empathetic point ratings 644 or other indicators associated with a variety of secondary factors 652 known to impact the patient's emotional reaction to care interactions (FIG. 12, 622) including, for example, payer data reflecting the estimated or known cost of care over predefined time periods such as 1 month, 3 months, and 12 months, which may indicate a seriousness of the patient's medical condition or needs, clinical data reflecting the patient's illness, lab results, and/or vitals, and social data including the patient's zip code, whether the patient smokes, consumes drugs, and/or drinks, as well as the patient's family status and/or ethnicity.

In some embodiments and as shown in FIG. 16B-16C, the neural network 638 and the machine learning algorithm(s) of the empathetic interaction module 122 and the neural network module 124 may additionally incorporate feedback from a post-interaction follow-up survey 650 gauging the patient's perception of the care interaction (FIG. 12, 624) to augment and improve the empathetic interaction module software's decision-making and propagate further machine learning for determinations made regarding the emotional reaction information 642, the empathetic point ratings 644, and the resulting empathy meter scores 646. Cumulatively, this survey feedback may be used to revise and improve the algorithm(s) of the empathetic interaction module 122 (FIG. 12, 626) regarding whether and when the patient felt/feels cared for by the provider and to collect data regarding whether the patient experienced an improvement or lack of improvement of an illness after the care interaction. Exemplary post-care-interaction survey questions may include, for example: (1) On a scale of one to ten, did you feel cared for by the doctor/provider; (2) If the score is 9-10, what did the doctor do to make you feel cared for; and (3) If score is 0-8, what could the doctor have done to make you feel more cared for? The answers provided may link to social media ratings and/or promotions for the provider 54, as well as be categorized for within the care network platform 200 regarding the provider's specialty and particular skills, which may then be used by the care match platform 400 in matching patients and providers. The survey answers may be provided to the doctor for real-time feedback that remains confidential, or they could be provided through the patient terminal 68 and shared with the medical group or medical director, depending the practice's style of coaching and feedback. Feedback from the post-interaction survey 650 may be structured to play to the provider's strengths within the patient's care network 115 to help foster a growth mindset for the care network platform 200, limiting resentment and optimizing new habit formation and learning amongst care team members.

In addition and as discussed above in relation to the care match subsystem 400, the emotional reaction information 642, the empathetic point ratings 644, and/or the empathy meter score(s) 646 may be used to further refine the ability for the care network platform 200 and the care match subsystem 400 to provide patients 52 with optimal care matches for future health care interactions as it provides an ongoing feedback loop and learning process (FIG. 12, 625) for identifying the person(s), the relationships, personalities, skillsets, price points, and circumstances that lead to positive care experiences. In this regard, the empathetic interactions subsystem 600 and its implemented neural network 638 and empathy meter 602 provide the ability to gauge future costs of care based on care interaction empathy meter scores 646 and whether a patient felt cared for based on the empathy meter. The empathetic interactions subsystem 600 may categorize data in the matching database 86 for further analysis and matching improvement. For example, historical emotional responses and subsequent survey information/ratings from patients may be categorized by diagnosis/illness, time, location, personality, and communication styles. This empathetic interaction information may then be used in conjunction with data on personality type and interpersonal communication style(s) from the care match subsystem 400.

In one operational embodiment, a proprietary and confidential database may be maintained by the healthcare provider and used to inform suggestions regarding which patients should see which providers to optimize the likelihood of a population feeling cared for by a group of available providers in the care network. The empathetic interactions subsystem 600 may provide suggestions for providers from whom a patient would be able to get the care they need addressed in the most economical and efficient way while feeling truly cared for.

Because the empathetic interaction subsystem 600 provides an ongoing feedback loop and learning process for identifying the patients, provider-patient relationships and matches, personalities, skillsets, price points, and care interaction circumstances that lead to positive care experiences, the subsystem enables a variety of care-improvement methods. In one embodiment of an improved method of patient care shown in FIG. 17 (660), the empathetic interaction module 122 may select for the patient 52 a set of questions from a list of personalized health questions 654 stored in the interaction database 88 of FIG. 1C (662). The selected questions may be deemed the most important or relevant questions for the patient 52, together with their medical issue and other secondary factors such as social data, clinical data, and payer data, to ensure a positive impact on the patient's health and to result in the patient feeling cared for. The set of personalized health questions may be provided to the healthcare provider prior to the care interaction via an appropriate GUI screen $128_{1-n}$ at the user terminal 68 used by the provider 54 (664). During the care interaction, the provider 54 may ask the set of questions (666) and receive answers (668), all while the empathetic interaction subsystem 600 performs its real-time evaluation and assignment of the empathy meter score(s) 646 for the patient 52, for the provider 54, and/or for the comprehensive interaction, as discussed above in relation to FIG. 12 (669). In this regard, the pre-selected set of personal health questions 654 may be evaluated for its efficacy in maximizing the empathy meter score(s) 646 for the care interaction, and the questions and their impact or affect become part of a feedback loop (670) that impacts future selection of the set of the personalized health questions, further improves the software of the empathetic interaction module 122 and the neural network module 124, as well as the care match module 116 and methods discussed above.

In another embodiment, the patient 52 may be presented with several personal healthcare or biographical questions via the terminal 68 operating at the patient 52 prior to the tele-health or in-person care interaction, thereby informing the provider 54 of information that may not typically be shared on a standard intake form or when discussing a standard chief complaint. Exemplary pre-care-interaction questions may include, for example: (1) What could we do to make you feel most cared for in your visit today; (2) What worries you the most; and/or (3) How confident are you in managing the medical issue(s) you are currently having?

The empathetic interactions subsystem 600 may also be implemented from the vantage point of the provider 54 to elevate human connection and morale and to maintain positive relationships between enrolled provider 54 colleagues and may continuously assess and/or monitor for healthcare provider burnout.

For example, regularly scheduled questions may be presented to providers 54, as set by a care group owner, medical group, or automatically via the empathetic interaction module 122. Exemplary questions for assessing provider job satisfaction may include: (1) Do you feel in control of your work; (2) Do you feel challenged in your work; and/or (3) Do you like the people you work with? Additional questions may be asked in relation to screening for emotional exhaustion and issues of depersonalization. Through the questions above, issues may be raised in an anonymous, but transparent way to the leadership of an enrolled provider group to help limit burnout and staff turnover, as well as to limit future poor care interactions resulting from the care provider staff not feeling cared for. In this regard, coaching sessions with videos and/or personalized coaching lessons from empathy professionals may be implemented via the empathetic interaction module 122, and provided to enrolled providers needing or desiring to develop new skills based on feedback from patients 52, other providers 54, and/or the provider assessment questions. In addition, the software 100 may be integrated with wellness and fitness applications to allow for access to self-care tools for enrolled providers in need of wellness support to improve their empathetic care capabilities.

In one embodiment, the emotional reaction information 642, the empathetic point ratings 644, and/or the empathy meter scores 646 may individually or together contribute to Hospital Consumer Assessment of Healthcare Providers and Systems (HCAHPS) metrics and other service, access, quality, and safety metrics that are provided to patients by Medicare, Medicaid, and/or other care payers or entities after a care encounter. The emotional reaction information 642, the empathetic point ratings 644, and/or the empathy meter scores 646 may also be made accessible to third-party digital health applications via the communication interface and the appropriate API(s). Similarly, the software 100 may be integrated with the existing electronic medical record to push and pull relevant medical data for optimizing empathetic care interactions with the whole care-provider team.

The empathetic interactions subsystem is configured with clear privacy and sharing options. Patients 52 and providers 54 may consent and "opt in" to sharing their data from virtual and in-person care interactions as collected by the tele-health tools 70 running on their terminals 68 such as, for example, smart phones, other mobile devices, and computers. In addition, data may be collected between multiple care interactions to statistically determine if and when positive emotional interactions appeared to occur, and under what circumstance a patient felt cared for, encompassing both online virtual visits using texting, video, or phone calls and in-person interactions in which audio and/or video is recorded. Transcription of in-person interactions may take place with audio and video recording tele-health tools that auto-populate and document in the medical record.

The tele-health networking, interaction, and care-matching system 50 and associated methods of use disclosed herein provide a number of overarching benefits over existing tele-health mechanisms:

Improved Patient Care: The system allows more people to feel cared for and better connects patients and care providers to optimize care interactions for better care. Ultimately, people are relatively fixed in who they are. By better matching patients and providers in the right circumstances, patients feel more cared for and providers receive more gratification from their work. If these outcomes take place, health care costs can be reduced while improving outcomes and the care experience for large populations as well as individuals.

Multi-Practice Engagement with Patients: Existing systems provide a practice-centric solution that connects the patient to one or more members of the practice organization. This excludes many people important to the patient who comprise the individual's support group/care team. The care network enables a better patient care experience by helping to unite all concerned and involved parties, improving the transfer of information and access to specialist knowledge.

Lightweight, Rapid Entry into Tele-health: The system assists top physician groups in launching several strategic service offerings that help build momentum toward large enterprise partnerships like population health in a Virtual IPA or Virtual Independent Physician Association.

Low Barrier to Entry for Provider Onboarding: By making provider signup easy, without significant cost and via trusted peer referrals, a quality care network of providers may exist upon a low-cost platform where economies of scale could be realized for optimizing care interactions and outcomes.

Confidential & Extensive Data Set: The methods for collecting and storing data about care interactions are confidential and passive, allowing for a larger dataset than is obtained manually by online survey companies and feedback processes.

Increased Provider Rating Accuracy: Care ratings online are often limited by the number of reviews and also are, at times, inaccurate relative to overall patient perceptions of a care provider. By enabling analysis via telemedicine and in-person emotion analysis, more data can be collected for making an accurate assessment for a better matching between patients and providers.

The system may be interoperable with ERM systems or an emerging standard for electronic medical records such as, for example, Apple's new standard. In addition, the system could be implemented as a peer-to-peer application relying on blockchain technology in recording interaction histories and data collection (e.g., personality assessment data, survey data, rating information, emotional reaction information). The system may also integrate automatic billing of insurance plans and analysis of a providers' network status with insurance, credentials, licensure and medical malpractice status. The system could also be applied to other professional, non-medical industries within which empathy and care between the provider and the customer are important and/or in which virtual meetings should be heavily looked or audited (e.g., financial service provider discussions).

Ultimately, embodiments of the network, interaction, and care-matching platform 50 and associated methods discussed herein optimizes empathetic care interactions on a personalized basis as well as large-scale population health basis to improve patient engagement, treatment adherence, the patient experience, the care team experience, health outcomes, and the cost of care.

Although the above embodiments have been described in language that is specific to certain structures, elements, compositions, and methodological steps, it is to be understood that the technology defined in the appended claims is not necessarily limited to the specific structures, elements, compositions and/or steps described. Rather, the specific aspects and steps are described as forms of implementing the claimed technology. Since many embodiments of the technology can be practiced without departing from the spirit and scope of the invention, the invention resides in the claims hereinafter appended.

What is claimed is:

1. An integrated tele-health networking, interaction, and care-matching system, comprising:
   a tele-health operations server operating one or more processors; a patient database, a provider database, a matching database, and an interaction database; and
   a management engine running on the tele-health operations server, the management engine executing a database management module, a rule module including a network module, a care match module, an empathetic interaction module, and a graphical user interface (GUI) module configured to display a GUI having a plurality of preconfigured, interactive screens to users operating at least a healthcare provider terminal, a patient terminal, a caregiver terminal, an advocate terminal, and a friend and family terminal, the management engine:
   receiving, via one or more emotional data elicitation tools associated with at least one of the healthcare provider terminal and the patient terminal, recorded interaction data for a patient reflecting a care interaction between a healthcare provider and the patient;
   determining, based on the recorded interaction data using a neural network, emotional interaction information reflecting a state of mind of the patient during the care interaction;
   based on a plurality of predefined empathetic criteria, rating the emotional reaction information;
   based on a plurality of secondary empathy factors including paver data, clinical data, and social data associated with the patient, rating the plurality of secondary empathy factors according to a know n statistical impact on care-interaction empathetic qualities;
   based on the rating of the emotional reaction of the patient and the rating of the secondary empathy factors, determining a real-time empathy meter score for the care interaction; and
   displaying the one or more of the empathy meter scores at one or more of the patient terminal and the provider terminal.

2. The integrated tele-health networking, interaction, and care-matching system of claim 1, the management engine further displaying, during the care interaction, via the GUI module, and upon one of the preconfigured, interactive screens at the patient terminal or the provider terminal, the real-time empathy meter score.

3. The integrated tele-health networking, interaction, and care-matching system of claim 1, wherein the recorded interaction data comprises one or more of a voice tone, a voice pitch, a voice pitch range, a voice volume, a speaking speed, a facial expression, a pattern of bodily movement, a posture, and a segment of discussion content.

4. The integrated tele-health networking, interaction, and care-matching system of claim 3, wherein the emotional reaction information comprises one or more of a frustration level, an anxiety level, an excitement level, a friendliness level, an anger level, a sadness level, a humor level, a happiness level, a presence of one or more key phrases, a comprehensive content quality, a quantification of questions asked, a quantification of statements made, a courteousness level, and an interest level.

5. The integrated tele-health networking, interaction, and care-matching system of claim 4, wherein the rating of the emotional reaction information comprises assigning, within a neural network, one or more numeric point ratings to the emotional reaction information, wherein a lowest point rating reflects a least empathetic interaction rating and a highest point rating reflects a most empathetic interaction rating.

6. The integrated tele-health networking, interaction, and care-matching system of claim 1, the management engine further:
   selecting, via the empathetic interaction module and from a plurality of healthcare questions stored in the interaction database, a set of personalized healthcare questions deemed relevant to the patient;
   providing, via the GUI module and the provider terminal, the set of the personalized healthcare questions to the healthcare provider for use during the care interaction;
   recording, via the one or more of the emotional data elicitation tools, a set of answers to the set of the personalized healthcare questions; and
   based on the set of the answers, selecting, via the empathetic interaction module and from the plurality of the healthcare questions stored in the interaction database, a next set of personalized healthcare questions deemed relevant to the patient.

7. The integrated tele-health networking, interaction, and care-matching system of claim 1, the management engine further:
   implementing a referral-based care network that connects the patient with the healthcare provider, one or more non-medical-provider caregivers, one or more healthcare advocates, and one or more family members or friends for the provision of tele-medicine services via the provider terminal, the patient terminal, the healthcare provider terminal, the advocate terminal, and the friend and family terminal.

8. The integrated tele-health networking, interaction, and care-matching system of claim 1, the management engine further:
   receiving, via the patient terminal, rating information and personality assessment information from the patient; and
   matching, based upon the rating information, the personality assessment information, and the emotional reaction information, the patient with an optimal healthcare provider for future care interactions with the patient.

9. A system for determining an empathetic quality of a care interaction between a patient and a healthcare provider, comprising:
   one or more emotional data elicitation tools associated with at least one of a patient terminal and a provider terminal;
   one or more databases storing patient data, provider data, care matching data, and care interaction data; and
   an empathetic interaction module running on an operations server and in communication with the patient terminal, the provider terminal, and the one or more of the databases, the empathetic interaction module:
   receiving, from the one or more of the emotional data elicitation tools, a stream of care interaction data recorded during the care interaction;
   determining, from the stream of the care interaction data using a neural network, an emotional reaction of the patient during the care interaction;
   rating the emotional reaction of the patient on a sliding scale from a least empathy experienced to a most empathy experienced;
   determining, based on the rating of the emotional reaction of the patient, one or more empathy meter scores reflecting the empathetic quality of the care interaction for the patient;
   rating a plurality of secondary empathy factors according to a know n statistical impact on care-interaction empathetic qualities, the plurality of the secondary empathy factors including payer data, clinical data, and social data associated with the patient;
   determining, based on the rating of the emotional reaction of the patient and the rating of the secondary empathy factors, the one or more of the empathy meter scores reflecting the empathetic quality of the care interaction for the patient; and
   displaying the one or more of the empathy meter scores at one or more of the patient terminal and the provider terminal.

10. The system of claim 9 wherein the determining and the displaying the one or more of the empathy meter scores occurs in real time during the care interaction.

11. The system of claim 9, wherein:
   the emotional data elicitation tools comprise one or more of a geographic information system (GIS), a voice recognition tool, and a facial recognition tool; and
   the care interaction data comprises one or more of a voice tone, a voice pitch, a voice pitch range, a voice volume, a speaking speed, a facial expression, and a segment of discussion content.

12. The system of claim 11, wherein the determining the emotional reaction of the patient comprises comparing the stream of the care interaction data recorded during the care interaction with a plurality of statistical data associated with one or more known human emotional states.

13. The system of claim 12, wherein the determining the emotional reaction of the patient comprises determining, for the patient during the care interaction, one or more of a frustration level, an anxiety level, an excitement level, a friendliness level, an anger level, a sadness level, a humor level, a happiness level, a presence of one or more key phrases, a comprehensive discussion content quality, an quantification of questions asked, a quantification of statements made, a courteousness level, and an interest level.

14. The system of claim 9, further comprising a network module running on the operations server and in communication with the one or more of the databases and the patient terminal, the provider terminal, a caregiver terminal, a healthcare advocate terminal, a friend or family member terminal, and one or more social networks, the network module implementing a referral-based care network that connects the patient with the healthcare provider, one or more non-medical-provider caregivers, one or more healthcare advocates, and one or more family members or friends for the provision of tele-medicine services via the provider terminal, the patient terminal, the healthcare advocate terminal, and the friend and family terminal.

15. The system of claim 9, further comprising a care match module running on the operations server and in communication with the patient terminal and the one or more of the databases, the care match module matching the patient with an optimal healthcare provider for the patient from among a plurality of healthcare provider options based on the one or more of the empathy meter scores and on care interaction rating information and personality assessment information provided by the patient and by each of the plurality of the healthcare provider options.

16. A method of scoring a healthcare interaction for empathy offered to a patient by a healthcare provider, the method comprising:
providing a tele-health operations server in communication with a storage system, a patient terminal, and a healthcare provider terminal, the tele-health operations server running a management engine that executes an empathetic interaction module, a care match module, and a graphical user interface (GUI) module;
receiving, via one or more emotional data elicitation tools associated with at least one of the patient terminal and the healthcare provider terminal, a stream of care interaction data recorded during the healthcare interaction, the care interaction data comprising one or more of a voice tone, a voice pitch, a voice pitch range, a voice volume, a speaking speed, a facial expression, and a segment of discussion content;
comparing, via the empathetic interaction module implementing a neural network, the stream of the care interaction data recorded during the healthcare interaction with a plurality of statistical data associated with one or more known human emotional states to associate one or more emotional reactions of the patient to the healthcare interaction with the stream of the care interaction data;
rating, via the empathetic interaction module based on a plurality of secondary empathy factors including payer data, clinical data, and social data associated with the patient, the plurality of secondary empathy factors according to a known statistical impact on care-interaction empathetic qualities together with the one or more of the emotional reactions on a sliding scale in which a lowest rating is associated with a least empathetic interaction and a highest rating is associated with a most empathetic interaction;
determining, via the empathetic interaction module and based on the rating of the one or more of the emotional reactions and the rating of the plurality of secondary empathy factors, one or more empathy meter scores reflecting the empathy felt by the patient from the healthcare provider; and
displaying the one or more empathy meter scores reflecting the empathy felt by the patient from the healthcare provider.

17. The method of claim 16, further comprising displaying, via the GUI module and upon at least one of the patient terminal and the provider terminal, an empathy meter screen depicting the one or more of the empathy meter scores.

18. The method of claim 17, wherein the rating the one or more of the emotional reactions, determining the one or more of the empathy meter scores, and displaying the one or more of the empathy meter scores occur in real time during the healthcare interaction.

19. The method of claim 16, further comprising:
matching, via the care match module and based upon the stream of the care interaction data, the one or more of the emotional reactions of the patient to the healthcare interaction, and the one or more of the empathy meter scores, the patient with a second healthcare provider.

* * * * *